(12) United States Patent
Siller-Jackson et al.

(10) Patent No.: US 6,544,548 B1
(45) Date of Patent: *Apr. 8, 2003

(54) KERATIN-BASED POWDERS AND HYDROGEL FOR PHARMACEUTICAL APPLICATIONS

(75) Inventors: Arlene J. Siller-Jackson, Helotes, TX (US); Mark E. Van Dyke, Fair Oaks Ranch, TX (US); Scott F. Timmons, San Antonio, TX (US); Cheryl R. Blanchard, San Antonio, TX (US); Robert A. Smith, Jackson, MS (US)

(73) Assignee: Keraplast Technologies, Ltd., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/638,643

(22) Filed: Aug. 14, 2000

Related U.S. Application Data

(63) Continuation-in-part of application No. 09/587,157, filed on Jun. 5, 2000, which is a continuation-in-part of application No. 09/528,893, filed on Mar. 20, 2000, now Pat. No. 6,270,793, which is a continuation-in-part of application No. 09/512,918, filed on Feb. 25, 2000, now Pat. No. 6,274,155, which is a continuation-in-part of application No. 09/394,782, filed on Sep. 13, 1999, now Pat. No. 6,316,598.

(51) Int. Cl.[7] ............................ A61F 13/00; A61K 7/06; A61K 9/00; A61K 6/00; A01N 25/34; A01N 37/18
(52) U.S. Cl. ...................... 424/449; 424/400; 424/70.1; 424/70.11; 424/70.12; 424/70.21; 424/70.22; 424/70.24; 424/70.27; 424/401; 424/402; 424/443; 514/2; 514/21
(58) Field of Search ........................... 424/70.1, 70.11, 424/70.12, 70.21, 70.22, 70.24, 70.27, 449, 443, 401

(56) References Cited

U.S. PATENT DOCUMENTS

| 4,135,942 A | 1/1979 | Kikkawa ...................... 106/155 |
| 4,357,274 A | 11/1982 | Werner ........................ 260/123 |

(List continued on next page.)

FOREIGN PATENT DOCUMENTS

| EP | 0454600 A | 10/1991 |
| JP | 56129035 | 10/1981 |

(List continued on next page.)

OTHER PUBLICATIONS

Blanchard, et al., U.S. application Ser. No. 09/057,161.
Southwest Research Institute Annual Report, 17–18, 21, 1997.

(List continued on next page.)

Primary Examiner—Thurman K. Page
Assistant Examiner—Isis Ghali
(74) Attorney, Agent, or Firm—Vinson & Elkins L.L.P.

(57) ABSTRACT

A hydratable, highly absorbent keratin solid fiber or powder capable of absorbing a large weight excess of water may be produced by partially oxidizing hair keratin disulfide bonds to sulfonic acid residues and reacting the sulfonic acid residues with a cation. The neutralized suspension can be filtered, washed, and dried, leaving keratin solid which can be shredded into fibers and further ground into powder. Addition of water to the solid produces a hydrogel. The powder or hydrogel may be useful as an absorbent material, as a therapeutic for skin, or as an excipient. The keratin materials can be incorporated into nonwoven films. The hydrogel can be used as a biocompatible viscoelastic filler for implant applications. Another use for the absorbent keratin and keratin hydrogel is as an excipient in pharmaceutical and cosmetic applications.

48 Claims, 12 Drawing Sheets

U.S. PATENT DOCUMENTS

| | | | |
|---|---|---|---|
| 4,369,037 A | 1/1983 | Matsunaga et al. | 8/127 |
| 4,439,417 A | 3/1984 | Matsunaga et al. | 424/70 |
| 4,495,173 A | 1/1985 | Matsunaga et al. | 424/70 |
| 4,570,629 A | 2/1986 | Widra | 128/156 |
| 4,751,074 A | 6/1988 | Matsunaga et al. | 424/70 |
| 4,839,168 A | 6/1989 | Abe et al. | 424/74 |
| 4,895,722 A | 1/1990 | Abe et al. | 424/71 |
| 4,959,213 A | 9/1990 | Brod et al. | 514/21 |
| 5,047,249 A | 9/1991 | Rothman et al. | 424/543 |
| 5,053,220 A * | 10/1991 | Arraudeau et al. | |
| 5,134,031 A | 7/1992 | Kagechi et al. | 428/373 |
| 5,258,043 A | 11/1993 | Stone | 623/66 |
| 5,276,138 A | 1/1994 | Yamada et al. | 530/357 |
| 5,358,935 A | 10/1994 | Smith et al. | 514/21 |
| 5,679,377 A * | 10/1997 | Bernstein et al. | |
| 5,712,252 A | 1/1998 | Smith | 514/21 |
| 5,763,583 A | 6/1998 | Arai et al. | 530/353 |
| 5,792,090 A | 8/1998 | Ladin | 602/48 |
| 5,824,331 A | 10/1998 | Usala | 424/424 |
| 5,932,552 A | 8/1999 | Blanchard et al. | 514/21 |
| 5,948,432 A | 9/1999 | Timmons et al. | 424/443 |
| 6,270,793 B1 * | 8/2001 | Van Dyke et al. | |
| 6,274,155 B1 * | 8/2001 | Van Dyke et al. | |
| 6,284,230 B1 * | 9/2001 | Sako et al. | |

FOREIGN PATENT DOCUMENTS

| | | |
|---|---|---|
| JP | 57109797 | 7/1982 |
| JP | 1197423 | 8/1989 |
| JP | 3011099 | 1/1991 |
| JP | 3294297 | 12/1991 |
| JP | 4312534 | 11/1992 |
| JP | 5285374 | 11/1993 |
| JP | 5285375 | 11/1993 |
| JP | 6116300 | 4/1994 |
| JP | 6293631 | 10/1994 |
| JP | 6336499 | 12/1994 |
| RU | 2106154 C1 | 3/1998 |

OTHER PUBLICATIONS

Technology Today, 16(3):9, 1995.

Timmons, et al., U.S. application Ser. No. 09/198,998.

Van Dyke, et al., U.S. application Ser. No. 09/330,550.

Yamauchi, et al., "Cultivation of fibroblast cells on keratin-coated substrata," Ploymers of Tissue Engineering, 329–40, 1998.

Atala, et al., "Injectable alginate seeded with chondrocytes as a potential treatment for vesicoureteral reflux," The Journal of Urology, vol. 150, 745–47, Aug. 1993.

Bellamkonda, et al., "Hydrogel–based three–dimensional matrix for neural cells," Journal of Biomedical Materials Research, vol. 29, 663–71 (1995).

Cao, et al., "Tissue–engineered nipple reconstruction," Plastic and Reconstructive Surgery, vol. 102, No. 7, 2293–98, Dec. 1998.

de Chalain, et al., "Bioengineering of elastic cartilage with aggregated porcine and human auricular chondrocytes and hydrogels containing alginate, collagen, and k–elastin," J. Biomed. Matter Res., 280–88, 1999.

Dillon, et al., "The influence of physical structure and charge on neurite extension in a 3D hydrogel scaffold," J. Biomater. Sci. Polymer Edn., vol. 9, No. 10, 1049–69 (1998).

Kang, et al., "Fabrication of porous gelatin scaffolds for tissue engineering," Biomaterials 20, 1339–44 (1999).

Plant, et al., "Axonal growth within poly (2–hydroxyethyl methacrylate) sponges infiltrated with Schwann cells and implanted into the lesioned rat optic tract," Brain Research 671, 119–130 (1995).

Santin, et al., "Synthesis and characterization of a new interpenetrated poly(2–hydroxyethylmethacrylate)–gelatin composite polymer," Biomaterials 17, 1459–67 (1996).

Sechriest, et al., "GAG–augmented polysaccharide hydrogel: A novel biocompatible and biodegradable material to support chondrogenesis," J. Biomed. Matter Res., 535–41 (2000).

Yu, et al., "A laminin and nerve growth factor–laden three–dimensional scaffold for enhanced neurite extension," Tissue Engineering, vol. 5, No. 4, 1999.

* cited by examiner

1:6 Solid to Liquid Ratio

1:8 Solid to Liquid Ratio

1:6 Solid to Liquid Ratio

1:4 Solid to Liquid Ratio

KERATIN-BASED POWDERS AND HYDROGEL FOR PHARMACEUTICAL APPLICATIONS

RELATED APPLICATIONS

The present application is a continuation-in-part of U.S. patent application Ser. No. 09/587,157 filed Jun. 5, 2000, which is a continuation-in-part of U.S. patent application Ser. No. 09/528,893 filed Mar. 20, 2000, now U.S. Pat. No. 6,270,793, which is a continuation-in-part of U.S. patent application Ser. No. 09/512,918, filed Feb. 25, 2000, now U.S. Pat. No. 6,274,155, which is a continuation-in-part of U.S. patent application Ser. No. 09/394,782 filed on Sep. 13, 1999, now U.S. Pat. No. 6,316,598.

FIELD OF THE INVENTION

The present invention is related generally to a keratin composition and method for making same. Specifically, the present invention relates to an absorbent keratin powder or fiber. More specifically, the present invention includes a hydratable keratin solid which forms a hydrogel upon addition of water for use in various applications including nonwoven films, diapers, skin treatments, prosthetic devices, excipients, tissue engineering scaffolds and the like. Active agents can be bound to the keratin excipient for controlled drug delivery.

BACKGROUND OF THE INVENTION

Absorbent materials are currently used to absorb body fluids such as urine, menses, and wound exudate. The absorbent materials are placed near the skin to serve this purpose. One class of products includes diapers, where the absorbent material can be derived from wood pulp, cellulosic fibers, or super absorbent, synthetically produced material. Diapers commonly have an inner core designed to absorb urine and water. The core is typically formed from a superabsorbent polymer dispersed in a larger amount of less absorbent material. The absorbent materials typically contained in the core are separated from the skin by at least one layer of material. The absorbent materials absorb urine and can become saturated. It is believed that some material from the absorbent core leaches from the wet absorbent and travels back to the skin. In the case of chemically treated absorbent materials and films, depending on the chemicals, the leachate may be irritating and is not believed to be beneficial. Skin contact with urine can also occur and result in irritation. This type of irritation may exacerbate diaper rash problems.

Other products which contain absorbent materials for use next to the skin include feminine hygiene products such as tampons and pads. These products serve to absorb menses. Another class of products using absorbent materials includes wound dressings, both those designed for humans, and dressings for veterinary use for application to wounds or skin irritations or disorders in animals. For specific applications, wound dressings preferably absorb exudate from wounds while keeping the wounds relatively moist to promote healing. In some applications, a gel may be desirable as a wound dressing, where the gel can maintain a moist wound environment, while absorbing excess exudate.

What would be desirable is an absorbent material formed from a natural product. What would be beneficial is a non-toxic product derived from natural sources that would cause no concern when leachate from the material contacts the body or the material itself contacts the body. What would be advantageous is a material that can absorb urine and, when wet, leach out a natural product that is beneficial with respect to diaper rash. What would be desirable is a material that can return a skin healing leachate to the skin. What would be desirable is a material that aids wound healing. What would be desirable is a hydrogel made of natural products formable by adding water to a powder or fiber. What would be desirable is a biocompatible carrier or excipient that could be used in the delivery of drug actives to various organs of the body. What would be desirable is a biocompatible carrier to which active agents can be bound and later released.

Tissue engineering is a rapidly growing field encompassing a number of technologies aimed at replacing or restoring tissue and organ function. The success of tissue-engineered implants rest on the invention of biocompatible materials that can act as cell-scaffolds and support cell growth. Of benefit are tissue-engineering scaffolds materials that are mitogenic or contain mitogenic factors. Such scaffolding materials can be used for in a wide array of tissue engineering implants containing cellular components, such as, for example, osteoblasts, chondrocytes, keratinocytes, and hepatocytes, to restore or replace bone cartilage, skin and liver tissue respectively.

SUMMARY OF THE INVENTION

The present disclosure addresses at least some of the deficiencies in the art by providing a hydratable, hydrogel-forming solid derived from a keratinous source such as hair, fur, human hair and the like. In the context of the present invention, the term "hydratable keratin" and "hydratable keratin material" is a keratin or keratin material that when hydrated can form a hydrogel. In the context of the present invention, the term "cross-linked insoluble oxidized keratin" means a network of cross-linked keratin containing sulfonic acid residues that is effectively of infinite molecular weight in that the molecular weight is approximated by the weight of the sample. Such networks may be viewed as being effectively one molecule. The status of a sample as being a "cross linked insoluble oxidized keratin" can be verified by the addition of a solvent in which an oxidized keratin monomer (prepared by breaking all cross-links) is soluble. A "cross-linked insoluble oxidized keratin" will swell upon addition of such a solvent, but will not enter solution despite agitation, heat and prolonged incubation unless and until the cross-linked insoluble oxidized keratin undergoes degradation to form lower molecular molecules. The cross-linked insoluble oxidized keratin preparation of the current invention may contain up to about 90 percent by weight of lower molecular weight polypeptides which may be soluble, but the insoluble character and gel forming are dependent upon network structure of the cross-linked insoluble oxidized keratin. The term "insoluble" refers to the properties of the of cross-linked oxidized keratin while it exists as a network of effectively infinite molecular weight. Upon hydrolysis, the cross-linked insoluble oxidized keratin network will enter into solution to the extent of degradation to lower molecular weight polypeptides. As this process ensues, molecules of finite molecular weight are generated which continue to hydrolyze and degrade to molecules of decreasing molecular weight. The solubility of these lower molecular weight polypeptides is enhanced by the fact that hydrolysis results in the generation of molecules that are more soluble by virtue of their low molecular weight (Flory, 1953). Solubility is further enhanced by the increasing relative molar percentage of amine and acid functional groups that are being generated as a result of the continued hydrolytic degradation. The rate of such degradation can be controlled by varying preparation parameters of the "cross-linked insoluble oxidized keratin" such as extent of oxidation and the solids content. When the solvent is water, a cross-linked insoluble oxidized keratin that has undergone the ion exchange process of the current invention will form a hydrogel.

In certain embodiments, a hydrogel-forming solid as disclosed herein may absorb up to 5 to 20 times its weight in water to form a hydrogel. Such a solid, as well as the hydrogel formed from the solid will be useful in various applications such as use as an absorbent with skin healing properties when incorporated into diapers, feminine hygiene products, wound dressings, including both human and veterinary uses, as a soft tissue augmentation medium when used in subdermal implants, tissue engineering cell scaffolds, as a moisture containing agent in cosmetics, oils, lotions, or gels for use on the skin, in applications related to the healing of damaged skin, and as a pharmaceutical excipient for sustained and/or controlled release pharmaceutical applications.

A hydratable keratin solid may be made by methods that include providing a keratinous material, or keratin, having disulfide linkages and partially or substantially oxidizing the keratinous material with an oxidizing agent, for example, such that some disulfide linkages are cleaved and oxidized, forming hydrophilic sulfonic acid or cysteic acid residues. A preferred source of keratinous material is human hair, although the keratin may be obtained from hair or fur of animals including any mammal, or from finger or toenail material or from hooves, feet, beaks, skin, feather or horns. Human hair is a preferred source of keratin because of its ready availability from cuttings of barber and beauty shops, because it is expected to be less prone to cause undesirable immune or allergic reactions in a human, and because a keratin preparation may be made from the hair of a subject for whom the preparation will be used. This last advantage can be especially important in embodiments involving subdermal and tissue engineering implantations.

It is well known in the art that keratins contain substantial sulfur, that is, the amino acid sequence of keratin contains a high proportion of cysteine residues as compared to proteins in general. These cysteines each include a sulfhydryl moiety that is able to bond with another sulfhydryl moiety from another cysteine residue to form a disulfide bond. The second cysteine may reside within the same keratin molecule, or in another keratin molecule. These disulfide bonds are responsible for much of the tertiary and/or quaternary structure of this class of proteins. A suitable oxidizing agent is able to break this disulfide bond and to oxidize one or both of the sulfhydryl moieties so that they are no longer able to form a disulfide. Such an oxidation is a part of the process of forming the keratin products of the present disclosure. Preferred oxidizing agents include, but are not limited to peracetic acid, hydrogen peroxide, perborates, percarbonates, benzoyl peroxide, or ammonium sulfate peroxide. However, any suitable oxidizing agent known in the art can be used in the practice of the invention. After oxidation, the liquid oxidizing agent can be filtered from the oxidized keratin solid, and the solid may be washed to remove residual oxidizing agent, for example.

The resulting solid may then be suspended in a non-aqueous solvent and the pH may be adjusted upward with base—conveniently to at least neutral pH. Preferred solvents for this second solution do not include more than about 20 volume percent water, as the water may hydrolyze the peptide backbone during processing. Preferred solvents would include alcohols such as methanol, ethanol, or propanol, for example, and would also include non-aqueous polar, water-miscible solvents such as acetone and tetrahydrofuran, for example. An effective solvent should be able to solvate a Lewis base and should also be able to provide a medium able to keep the keratin sufficiently swelled to allow ionic associations or interactions between the base cations and anionic sulfonic acid groups in the keratin. Small amounts of water will assist in this regard, so blends of the aforementioned solvents in combination with water up to 20 volume percent may be used. Preferred bases include, but are not limited to sodium hydroxide, potassium hydroxide and ammonium hydroxide, which, as is known in the art, would yield or produce sodium, potassium and ammonium cations, respectively, upon entering solution.

The keratin suspension may be heated, and is preferably heated to boiling for a time sufficient to swell the keratin. The keratin suspension may be stirred without heat for a longer period of time to allow a more complete association or reaction between the sulfonic acid groups and the base cations. The continued reaction time at or near room temperature, or even below room temperature while stirring is contemplated by the inventors to allow the base cations to approach and bind to the keratin anionic sites with a lower incidence of peptide backbone degradation that could occur with continued boiling. The cations for use in the present invention, therefore, must be able to interact with the anionic cysteic groups in the keratin material. The use of the term "cations" or "monovalent cations" in the present disclosure and claims is indication of those cations that are able to do so. Salts of aspartate and glutamate may also be present in high concentration and will contribute to the absorbency of the hydratable keratin material. After a sufficient reaction time, the keratin solid may be removed from the suspension by filtration, for example, and dried, leaving a solid salt formed of the keratin sulfonic acid or cysteic acid groups and base cations. This solid may be shredded into a fibrous form and/or ground into a finely divided powder. This solid may be used in certain embodiments, or it may be hydrated by adding water, for example, and the hydrogel, or viscoelastic hydrogel thus formed may be used in certain embodiments.

In certain embodiments, an absorbent keratin layer may be incorporated into various absorbent articles such as a disposable diaper, a wound dressing, or feminine hygiene product, by adsorbing or coating a keratin solid or hydrogel onto a layer of the article, by impregnating a component of such an article, or by associating a keratin material with a nonwoven layer of such an article. In certain embodiments an absorbent keratin powder may be applied directly to skin to absorb moisture and inhibit rashes or chafing, such as diaper rash, for example. A hydratable keratin solid of the invention may have an absorbency of 1, 5, 10, 15 or even up to 20 times its weight in water. The absorbency may be adjusted by, for example, varying the degree of oxidation of the keratin in the process. It may thus provide a substitute or a supplement for products such as talc and cornstarch. The inventors have demonstrated, for example, that a fibrous or powdered form of solid keratin material as described herein can absorb about 10 times its weight in water in about 10 seconds.

The hydratable keratin solids as described herein form a hydrogel or a viscoelastic hydrogel upon application of water, and also are contemplated to contain skin healing peptides associated with the keratin, which may leach out of the keratin products when wet. The keratin products thus provide an added benefit, in addition to water absorbency, that is, healing or soothing peptides are also released that may have beneficial effects on the skin of a user of the products. This property offers certain benefits in embodiments such as wound dressings, as well as cosmetics, gels or lotions for application to the skin.

In certain embodiments a keratin absorbent as disclosed herein may be used as a wound dressing material to absorb wound exudate by direct application, or by incorporation into a dressing. The solid, hydratable forms of keratin offer certain advantages in such applications because they may be stored as dry powders or fibers and hydrated to form a gel in the field, or only as needed, for example. Medical applications, such as wound exudate management or drug release, can make use of the keratin material in absorbent powder, fiber, woven fiber, or felt form.

The keratin hydrogel is also believed to be suitable for use as an implant filler, for example, used to fill a breast implant, or to augment soft tissue for cosmetic, reconstructive or aesthetic reasons, or in a tissue expander application. The keratin product may also be used in cosmetics to retain moisture next to the skin. The performance of cosmetics which reduce the greasy appearance of skin can be enhanced through the use of moisture absorbent keratin material as an additive or base ingredient, for example, in a cosmetic formulation. The keratin absorbent and hydrogel can also be used for a variety of tissue engineering applications. Both materials may act as biocompatible scaffolds that provide a mitogen, the keratin peptide, to the cellular components of a tissue-engineered implant. In the case of a keratin hydrogel tissue engineered implant, the degradation of keratin to lower molecular weight peptides can be controlled through a combination of processing and formulation parameters. As with other materials known in the art, the degradation rate is directly related to the rate of resorbtion in-vivo (Agrawal, 1997). Therefore, the resorbtion rate of the keratin hydrogel can be directly controlled.

The present invention may be described, therefore, in certain aspects as a composition comprising a hydratable keratin solid, wherein the solid comprises a keratin where at least a portion of the cysteic groups of the keratin are ionically or electrostatically associated with, or may be ionically bound to cations. As used herein, ionically bound or ionically associated would have their ordinary meaning as is known in the art, and would include the electrostatic attraction between an anion and a cation, and would include such interactions directly, such as through formation of ionic bonds, and interactions through intermediary bipolar moieties, for example. A cysteic group would include cysteine and derivatives of cysteine including cysteine and cysteic acid or sulfonic acid. As used herein, cysteic acid and sulfonic acid denote a cysteine side chain in which the terminal sulfur is bonded to three oxygen atoms to produce the sulfonic acid ion, $SO_3^-$, or the acidic form, $SO_3H$. In certain embodiments, a portion of the cysteic groups are oxidized to sulfonic acid or cysteic acid groups. Sulfonic acid or cysteic acid groups may comprise a significant portion of the total cysteic groups and in some embodiments the sulfonic acid groups may constitute a major portion of the total cysteic groups. The extent of the oxidation may be adjusted by adjusting certain parameters of the oxidation reactions, such as temperature, concentration of oxidizing agent, and time of reaction, for example, to achieve a product with certain desired properties, such as absorbency or resiliency, for example.

In certain embodiments, therefore, the present invention may be described as a hydratable keratin solid made by a process comprising oxidizing a portion of the cysteic acid groups of a keratin to obtain a keratin having oxidized cysteic groups, and contacting the keratin having oxidized cysteic groups with monovalent cations under conditions effective to form ionic associations or ionic bonds between at least a portion of the oxidized cysteic groups and the cations.

In some embodiments, the hydratable keratin solid is made by a process comprising oxidizing at least a portion of the cysteic acid groups of a keratin to obtain a keratin having oxidized cysteic groups, and contacting said keratin having oxidized cysteic groups with monovalent cations under conditions effective to form ionic associations or ionic bonds between a substantial portion of said oxidized cysteic groups and said cations. The oxidation may comprise placing the keratin in a solution containing a concentration of an oxidizing agent effective to oxidize a portion of the cysteic acid groups. The portion of oxidized cysteic groups may be a major portion of the total cysteic acid groups.

In certain embodiments of the present invention, the oxidation comprises placing the keratin in a solution containing a concentration of hydrogen peroxide, peracetic acid, perborates, percarbonates, benzoyl peroxide or ammonium sulfate peroxide effective to oxidize a portion of the cysteic groups.

The process of the present invention may further comprise heating the keratin solid containing oxidized cysteic groups in a solvent solution containing a dissolved base, wherein the base produces the monovalent cations in the solution. The solvent solution may comprise a solvent selected from methanol, ethanol, propanol, ether, tetrahydrofuran (THF), acetone, propylene glycol, 1,4-dioxane, and glycol ether, or combinations of these with up to 20 volume percent water. In certain embodiments the process further comprises removing the solution from the heat and stirring for a time effective to form ionic bonds between the cysteic groups and cations produced by the base. The process may also further comprise drying the keratin solid, such as by drying a solid or solution under vacuum.

Another aspect of the present invention is a composition comprising a keratin hydrogel wherein the hydrogel is produced by adding water to a composition comprising a hydratable keratin solid, wherein the solid comprises a keratin where at least a portion of the cysteic groups of the keratin are ionically bound to cations. In some embodiments, the composition of the present invention comprises a keratin viscoelastic hydrogel produced by adding water to a composition comprising a hydratable keratin solid, wherein the solid comprises a keratin where a portion of the cysteic groups of the keratin are ionically bound to or associated with cations.

Another aspect of the present invention is a process for making a hydratable keratin solid comprising: (1) oxidizing keratin in a first solution comprising a soluble oxidizing agent, such that a portion of the disulfide bonds of the keratin are oxidized to form sulfonic acid residues, to obtain an oxidized solid fraction; (2) separating the oxidized solid fraction from the first solution; (3) contacting the oxidized solid fraction with a second, basic solution comprising a monovalent cation dissolved in a solvent or solvent mixture; (4) maintaining the second solution containing the oxidized solid fraction and the monovalent cations for a time and at a temperature effective to allow an interaction between the sulfonic acid residues and the monovalent cations to obtain a salt solution of the keratin and the monovalent cation; and (5) substantially removing the solvent from the salt solution to obtain a pure hydratable keratin solid.

The process may also further comprise adjusting the pH of the second solution, to obtain a substantially neutral solution. In some embodiments, the keratin is obtained from hair, fur, skin, feet, beaks, horns, hooves or feathers and is preferably obtained from human hair.

In some embodiments, the keratin is oxidized by suspending the keratin in a solution of a suitable oxidizing agent such as one selected from the group consisting of hydrogen peroxide, peracetic acid, perborates, percarbonates, benzoyl peroxide, and ammonium sulfate peroxide, in a concentration of between about 1 and about 35 weight/volume percent. In various embodiments, the keratin is oxidized by suspending the keratin in a solution of an oxidizing agent selected from the group consisting of hydrogen peroxide, peracetic acid, perborates, percarbonates, benzoyl peroxide, and ammonium sulfate peroxide, in a concentration of about 1, or about 2, or about 3, or about 4, or about 10, or about 15, or about 20, or about 30, or about 32, or about 35 weight/volume percent. As used herein the term weight/volume percent refers to a solution in which the concentration is determined in weight percent, that is then diluted into a particular volume, arriving at a weight/volume percent. For example, in order to arrive at the oxidant solutions described herein a "stock solution" at fairly high concentration is diluted in water. As an example, hydrogen peroxide may be purchased as a 30 weight % solution (30 grams of peroxide per 100 grams of solution). To make 1 liter of a 2% solution of this, one would dilute 66.7 mL of the 30 weight % stock solution in 933.3 mL of water. The net effect is to cut the stock solution 15-fold (from 30 down to 2%). This ratio is a weight to volume ratio, so the resulting solution is described as 2 weight/volume %.

In some embodiments, the keratin is oxidized by suspending the keratin in a solution of a suitable oxidizing agent, such as one selected from the group consisting of hydrogen peroxide, peracetic acid, perborates, percarbonates, benzoyl peroxide, and ammonium sulfate peroxide, in a concentration of between about 1 and about 35 weight/volume percent, at a temperature between about 0° C. and about 100° C. In other embodiments the temperature is between about 4° C. and about 90° C., or between about 20° C. and about 100° C., or between about 80° C. and about 100° C. In other embodiments, the temperature is about 4° C., or about 90° C., or about 100° C.

The present invention may also include the process wherein the keratin is oxidized by suspending said keratin in a solution of an oxidizing agent selected from the group consisting of hydrogen peroxide, peracetic acid, perborates, percarbonates, benzoyl peroxide, and ammonium sulfate peroxide, in a concentration of between about 1 and about 35 weight/volume percent, at a temperature between about 0° C. and about 100° C. for a period of between 0.5 and about 24 hours, or in a concentration of oxidizing agent of between about 1 and about 35 weight/volume percent, at a temperature between about 0° C. and about 100° C. for a period of between 1 and about 2 hours, or for between about 2 and about 4 hours, or for between about 1 and about 4 hours, or for a period of about 10 hours.

More specifically, the present invention may include oxidizing the keratin by suspending the keratin in a solution of between about 1 percent to about 32 percent peracetic acid at a temperature between about 0° C. and about 100° C. for between about 0.5 and about 24 hours, or by suspending the keratin in a solution of about 1 percent peracetic acid at a temperature between about 0° C. and about 100° C. for between about 0.5 and about 24 hours, or by suspending the keratin in a solution of between about 4 percent peracetic acid at a temperature of about 4° C. for 24 hours, or by suspending the keratin in a solution of about 4 percent peracetic acid at room temperature for about 24 hours, or by suspending the keratin in a solution of about 4 percent peracetic acid at about 90° C. for about 10 hours, or by suspending the keratin in a solution of about 4 percent peracetic acid at a temperature between about 20° C. and about 100° C. for between about 1 and about 4 hours, or by suspending the keratin in a solution of about 4 percent peracetic acid at a temperature between about 80° C. and about 100° C. for between about 1 and about 2 hours, or even by suspending the keratin in a solution of about 2 percent peracetic acid at a temperature between about 0° C. and about 100° C. for about 2 hours.

A second solution in the process of making the disclosed compositions, wherein the second solution contains the oxidized solid fraction and monovalent cations may be heated, and may also be boiled for between about 0.5 hours and about 12 hours, for between about 0.5 hours and about 3 hours, or for about 1 hour. Once said solution is boiled, the solution may be allowed to continue reacting while being stirred after removal of the heat. Alternatively, the solution may be stirred and allowed to react without the application of heat, or of boiling temperatures. In certain embodiments, the solution is allowed to react at a temperature of between about 15° C. and about 30° C. for a period of between about 1 and about 24 hours, or at a temperature of between about 20° C. and about 25° C. for a period of between about 1 and about 5 hours, or at room temperature for a period of about 5 hours. In certain preferred embodiments the solution is heated to the boiling point of the solvent and boiled for 2 hours.

Certain processes as described herein are effective to produce a hydratable keratin solid, and it is an embodiment of the present invention that those solids may be hydrated by the addition of water to obtain keratin hydrogels, or even viscoelastic keratin hydrogels. The terms hydrogel and viscoelastic hydrogel, as used herein, are meant to have the art recognized definition, and could be described as absorbing water such that the water cannot be removed by mechanical methods such as pressure or centrifugation. Viscoelastic hydrogels would also be defined as gels that display non-Newtonian fluid properties.

In certain embodiments the present invention may be described as a disposable diaper that includes a hydratable keratin solid, or a diaper which incorporates a hydratable or absorbent keratin solid. A hydratable keratin solid may be coated on a layer of the diaper, either a layer next to the skin of a wearer, or a layer separated from the skin of a wearer by a water permeable layer. In certain embodiments a hydratable keratin solid may be associated with a nonwoven layer of a diaper, or may be impregnated into a layer of a disposable diaper, or it may be contained in an inner absorbent core.

In certain alternative embodiments, the present invention may be described as a feminine hygiene product, or a wound dressing that includes a hydratable keratin solid. As was described for use in diapers, a hydratable keratin may be coated on a layer of a product, associated with a nonwoven layer of a product, or even impregnated into a layer of a product or contained in an absorbent core. Exemplary products would include wound dressings, tampons, and sanitary pads. Wound dressings include absorbent wound dressing, that is dressing capable of, but not limited to, absorbing wound exudate and blood. Absorbent dressings include, but are not limited to, adhesive bandages. Adhesive bandages typically comprise an absorbent pad, a backing and a pressure sensitive adhesive to maintain the dressing in place. In one aspect of the present invention, an absorbent wound dressing comprising hydratable keratin is an absorbent pad of an adhesive bandage. In one embodiment, the hydratable keratin in such an absorbent pad is in a nonwoven film.

Certain embodiments of the invention may be described as methods for promoting healing of skin in a subject including a human or an animal having damaged skin, including providing an absorbent, keratin material, wherein a portion and preferably a substantial or major portion of the cysteic groups of said keratin are oxidized and wherein water soluble peptides are associated with the keratin, wherein at least some of said peptides can leach out from said keratin upon application of water, and wherein said peptides promote healing of damaged skin; and disposing the absorbent keratin material near damaged skin, such that moisture causes at least some of said peptides to leach out of said keratin and to contact said skin. The method may be practiced with animal or human subjects, such that either animal or human skin is healed by this method. The practice of the method for promoting skin healing as described herein may include the treatment of damaged skin including, but not limited to diaper rash, burn, sunburn, cut, abrasion, puncture, a sore, bed sore, ulcer, diabetic ulcer, irritated skin, surgical incision, skin graft donor site, or wrinkled skin. The keratin material may be incorporated in a nonwoven film. The nonwoven film may comprise synthetic polymer webs and may also comprise natural materials such as cotton. It is understood that in the practice of such embodiments, the wound of the subject being treated may exude or excrete moisture and that the absorption of such moisture by said keratin may cause the release of water soluble peptides from keratin products of the present invention.

In certain embodiments the present invention may be described as a method for promoting skin healing, in particular in those embodiments in which a keratin solid or hydrogel as described herein, such as a keratin solid or hydrogel in which the keratin is obtained from human hair, for example, is contained in, or forms a portion of a cream, lotion, or gel for application to skin, hair, lips, or nails, for example. Such formulations can offer various advantages such as moisturizing the skin, or inhibiting loss of moisture from the skin, as well as providing the healing effects of peptides that may leach from the keratin containing product. Such creams, lotions and gels may be applied to damaged skin, such as dry, burned, sunburned, wrinkled, cut, scraped, chapped, irritated, ulcerated or otherwise damaged skin or other tissue.

One aspect of the present invention is a nonwoven film composition comprising a synthetic polymer and a keratin material, wherein the keratin material has been oxidized and contains sulfonic acid groups. The keratin material may be oxidized keratin material that has not undergone the ion exchange process or may be oxidized keratin that has undergone the ion exchange process to form a hydratable keratin. In the latter, the sulfonic acid groups of the hydratable keratin are associated with monovalent cations. The keratin materials may also be associated with pharmaceutical agents which may be in the form of polar compounds which are capable of binding or otherwise associating with the keratin. Such a pharmaceutical agent is asprin. The synthetic polymer may be, but is not limited to, α-olefins, acrylates, urethanes, acetates, nylons, esters, and copolymers thereof. An α-olefin is considered to be any monomer containing an α-double bond. The nonwoven composition may also further comprise a natural material which may be, but is not limited to, cotton. In some embodiments of the invention, the nonwoven composition is a laminate, which may be, but is not limited to, a tri-laminate comprising two outer layers of synthetic polymer and a middle layer of keratin material. The keratin material in the middle layer may be partially exposed by openings in the two outer nonwoven synthetic polymer layers. In some embodiments of the invention the synthetic polymer layers are nonwoven webs of polymer fibers. In other embodiments, the synthetic polymer layers are woven webs of polymer fibers.

Another aspect of the invention is a nonwoven tri-laminate composition comprising a middle layer of a keratin material between two outer layers of synthetic polymer material. The synthetic polymer may be in the form of a nonwoven web. The keratin material may be oxidized keratin that contains sulfonic acid residues. The oxidized keratin may be subjected to ion exchange such that the keratin material is a hydratable keratin material. The keratin material may be associated with pharmaceutical agents, which may be in a cationic form. The synthetic polymer may be, but is not limited to, α-olefins, acrylates, urethanes, acetates, nylons, esters, and copolymers thereof. The synthetic polymer may be, but is not limited to, poly(hydroxy acids) such as polylactic acid, polyglycolic acid, or a copolymer thereof. The nonwoven composition may also further comprise a natural material which may be, but is not limited to cotton.

One aspect of the invention is a process for making a nonwoven film. In one embodiment a keratin material is applied to a first nonwoven web layer of synthetic polymer. A second nonwoven web layer of synthetic polymer is applied over the keratin material so as to form a tri-laminate composition with two outer layers of nonwoven synthetic polymer web and a middle layer of keratin material. Another aspect of the invention is a product made by the above described process. The keratin material may be oxidized keratin that contains sulfonic acid residues. The oxidized keratin may be subjected to ion exchange such that the keratin material is a hydratable keratin material. The keratin material may be associated with pharmaceutical agents, which may be in a cationic form. The synthetic polymer may be, but is not limited to, α-olefins, acrylates, urethanes, acetates, nylons, esters, and copolymers thereof. The nonwoven composition may also further comprise a natural material which may be cotton. The keratin material in the middle layer may be partially exposed by openings in the two outer nonwoven synthetic polymer layers.

Other aspects of the present invention include wound dressings, diapers and feminine hygiene products which comprise a nonwoven film made from a synthetic polymer and a hydratable keratin material. In certain embodiments, the non-woven film of the present invention may be next to the skin or other epithelial layer of a subject, or may be separated from the skin or other epithelial layer of a subject by a water permeable layer, which may be a non-wetting water permeable layer. In certain embodiments a hydratable keratin solid may be associated with a nonwoven layer of a diaper, or may be impregnated into a layer of a disposable diaper, or it may be contained in an inner absorbent core. These products may be laminate compositions, which may be tri-laminates comprising two outer layers of synthetic polymer and a middle layer of keratin material. The keratin material in the middle layer may be partially exposed by openings in the two outer nonwoven synthetic polymer layers. In some embodiments of the invention the synthetic polymer layers are nonwoven webs of polymer.

Creams, lotions, or gels of the present invention may incorporate or replace other ingredients known in the art, including, but not limited to oleaginous, emulsifiable, emulsion base, or water-soluble ointment bases as are well known in the pharmaceutical arts. Oleaginous bases that may be combined with the keratin compositions include ointments containing white wax and/or white petrolatum, ointments containing yellow wax and petrolatum, cetyl esters wax, oleic acids, and paraffins. Absorbent ointment bases or emulsifiable bases that may be used include those containing anhydrous lanolin, or combinations of cholesterol, stearyl alcohol, white wax and petrolatum, for example. Emulsion bases and components that may be used include ointments containing cetyl alcohol, and cold creams such as those containing cetyl esters wax, white wax, mineral oil, sodium borate and water, for example. Other ointments of the present invention may contain glyceryl monostearate, lanolin, stearic acid, or a combination of methylparaben, propylparaben, sodium lauryl sulfate, propylene glycol, stearyl alcohol and white petrolatum, for example, or an ointment containing cetyl esters wax, white wax, almond oil, sodium borate, stronger rose water, and rose oil, for example. Water soluble ointments and creams for use in the present invention may include glycol ethers and derivatives thereof, polyethylene glycols, polyoxyl 40 stearate, and/or polysorbates.

The preparations as described herein for topical applications may also include protectives and absorbents, demulcents such as benzoin, hydroxypropyl cellulose, hydroxypropyl methylcellulose, polyvinyl alcohol, propylene glycols, sodium alginates, and tragacanth. Emollients, astringents, or antiperspirants may also be included in the keratin containing formulations as described herein.

An aspect of the present disclosure is a method for augmenting soft tissue in a subject comprising injecting a keratin composition as described herein subdermally in an area in need of augmentation. A variety of such applications are available in light of the present disclosure and would include augmentation of soft tissue including, but not limited to bulking of a urinary sphincter in order to alleviate urinary incontinence, augmentation of vocal chords to restore elasticity, as well as improvement of the appearance of a subject by augmentation of breasts, lips, chin, gluteal area, or even to improve wrinkled or acne scarred skin, or skin scarred by other conditions, and including soft tissue voids or indentations. A keratin composition may be provided as a dry solid and hydrated after subdermal implantation, or a hydrogel or viscoelastic hydrogel may be prepared and implanted. In certain embodiments, a dry or hydrated keratin material may be contained in a biocompatible envelope, bag, or container for subdermal implantation, and hydrated after implantation by addition of water or absorption of body fluids, or a keratin material may be suspended in an injectable carrier and injected in the desired area of augmentation. In one embodiment, soft tissue augmentation is accomplished by injecting a preparation comprising a keratin hydrogel and a cell population.

Another aspect of the present invention is the use of keratin compositions for tissue engineering applications. One embodiment is an implantable preparation comprising a keratin hydrogel and a cell population. The cell population may include, but are not limited to, keratinocytes, fibroblasts, chondrocytes, hepatocytes, splenocytes, neurocytes, osteoblasts, or endothelial cells. The keratin hydrogel preparation may be prepared such that it is implantable by injection. Through processing and/or formulation parameters, the keratin hydrogel may be prepared such that is resorbable and that such resorption is at a controlled rate. The keratin hydrogel may be prepared such that it is resorbed upon implantation after about 150 days, or about 100 days, or about 90 days, or about 80 days, or about 70 days, or about 60 days, or about 50 days, or about 40 days, or about 30 days, or about 20 days, or about 10 days, or between about 10 and about 90 days, or between about 20 and about 90 days, or between about 50 and about 90 days, or greater than 90 days. The keratin hydrogel may also contain a therapeutic agent, which may be a water soluble peptide, which may be a mitogen.

Another embodiment is a cell scaffold comprising a nonwoven film which comprises a hydratable keratin which contains sulfonate groups. The nonwoven film may comprise a synthetic polymer which may be resorbable. The hydratable keratin may also be made resorbable, thereby rendering the entire nonwoven film resorbable. The nonwoven film may also be a laminate composition. The hydratable keratin may contain a therapeutic agent which may be a water soluble peptide, which may be a mitogen.

Another embodiment of the present invention is a method of implanting a preparation comprising a population of cells and a keratin hydrogel into an animal. The cell populations may include, but are not limited to, keratinocytes, fibroblasts, chondrocytes, hepatocytes, splenocytes, neurocytes, osteoblasts, or endothelial cells. The hydrogel may contain a therapeutic agent which may be a water soluble peptide, which may be a mitogen. A further embodiment is a method of implanting a cell scaffold comprising a nonwoven film that comprises a hydratable keratin which contains sulfonate groups. Cells may be grown on the nonwoven cell scaffold in vitro. Thereby, the nonwoven cell scaffold may be seeded with cells prior to implantation. Such cells include, but are not limited to, keratinocytes, fibroblasts, chondrocytes, hepatocytes, splenocytes, neurocytes, osteoblasts, or endothelial cells. The nonwoven cell scaffold may be used to repair damaged hard and soft tissues. Hard tissues include, but are not limited to, bone and cartilage. Soft tissues include, but are not limited to, skin, mucosa and muscle. Mucosal tissue includes, but is not limited to, gingival tissue, which may be damaged bone or damaged cartilage. Another embodiment comprises implanting a keratin hydrogel cell scaffold. A therapeutic agent may be included in the keratin component of all the cell scaffolds of the present invention. Such a therapeutic agent may leach out of the keratin and may be a water soluble peptide, which may be mitogenic.

On one aspect of the present invention, the keratin composition is a preparation comprising a cross-linked insoluble oxidized keratin excipient. The preparation may be in the form of a powder, tablet, film, capsule, lotion, cream, gel, solution, suspension, emulsion or aerosol. The preparation may be a cosmetic preparation or may be a pharmaceutical preparation. The preparation may further comprise one or more additives such as diluents, fillers, lubricants, stabilizers, binders and gelants.

It is an aspect of the present invention that a keratin composition as described herein, and in particular keratin obtained from human hair is also useful as an excipient for the delivery of an active agent. An embodiment of the invention may be described, therefore, as a composition comprising a keratin having oxidized cysteic groups and an active agent or as a cross-linked insoluble oxidized keratin excipient with an active agent. In certain embodiments the active agent is physically or sterically entrapped within the keratin excipient and released over time by diffusion, or as a keratin excipient is degraded. Further, in some embodiments the active agent may be associated with the keratin excipient. The association between the active agent and the keratin excipient may be by non-covalent attraction or association, through electrostatic, hydrophilic or ionic interaction, for example, or it may be covalently attached to a keratin excipient by covalent bonding to an oxidized keratin as described herein. In one embodiment, the active agent is in a cationic form that ionically binds to the sulfonate groups of the ionized keratin. In another embodiment the active agent is associated with the keratin excipient by Van der Waal's forces. Association of the active agent with a keratin excipient allows for the sustained and/or controlled release of active agents. In some embodiments, the controlled release of the active agent is provided by the hydrolysis of the keratin excipient. Such a formulation may include a hydratable keratin solid excipient, or a keratin hydrogel depending on the particular application. In some embodiments the active agent is a pharmaceutical agent while in other embodiments the active agent is a cosmetic agent.

In the practice of the invention, a dry hydratable keratin as described herein may be mixed with a powdered pharmaceutical agent and water added to hydrate the mixture, or alternatively such a solid mixture may be formulated as a compressed tablet to be orally administered or for extemporaneous preparations for injection, or as a molded tablet, or it may be enclosed in a capsule for oral administration or subdermal implantation, for example. In certain embodiments a solution containing a water soluble drug or pharmaceutical agent may be added to a hydratable keratin so that the agent is carried into a hydrogel along with the water. A prepared hydrogel, or dry formulation may also be enclosed in a digestible or biodegradable capsule, such as a hard gelatin capsule for oral administration. In certain embodiments, the described pharmaceutical preparations may be formulated for injection, either intravenous, subcutaneous, or intramuscular, for example, or for inhalant, for eye, ear, or nose drops, or for administration as a suppository.

It is understood that the pills formulated for oral administration, including a hydratable keratin solid, or even pills, capsules or tablets containing a keratin hydrogel may contain ingredients to serve as coatings, additional fillers, binders and for color coding purposes. These ingredients are in common use in present pharmaceutical formulations and may include, but are not limited to, gelatin, lactose, corn starch, calcium phosphate, povidone, magnesium stearate, stearic acid, colloidal silicon dioxide, hydroxypropyl methylcellulose, polyethylene glycol and one or more of the following dyes: FD&C Blue No. I Lake, FD&C Blue No. 2 Aluminum Lake, D&C Green No. 5, D&C Yellow No. 10, FD&C Yellow No. 6 or FD&C Red No. 3. Of course these are only exemplary fillers and dyes, those of skill in the art will recognize that other inactive ingredients may be used in the preparation of the formulations of the present invention.

Keratin excipient preparations as described herein may be prepared for oral administration, and would also include injectable solutions or suspensions for intramuscular or subcutaneous implantation including long acting injections, suppositories, topical ointments, transdermal applications such as skin patches, and preparations delivered by inhalation. Other ingredients may include a surfactant, such as hydroxypropylcellulose. Dispersions can also be prepared in glycerol, liquid polyethylene glycols, and mixtures thereof and in oils. Under ordinary conditions of storage and use, these preparations may contain a preservative to prevent the growth of microorganisms. Keratin excipient preparations may also include other compounds such as diluents, fillers, lubricants, stabilizers, binders and gelants. Diluents and fillers are added to increase bulk formation, and lubricants to reduce friction during the tableting or other formulation process. Binders are used in tableting and provide the cohesiveness necessary for bonding together the ingredients under compression. They also increase the strength of the compressed tablet and decrease its friability, leading to an improvement in the both appearance and mechanical characteristics.

The pharmaceutical forms suitable for injectable use include sterile aqueous solutions or dispersion, sterile powders and hydrogels for the extemporaneous preparation of sterile injectable solutions, dispersions or gels. The carrier can be a solvent or dispersion medium containing, for example, water, ethanol, polyol (for example, glycerol, propylene glycol, and liquid polyethylene glycol, and the like), suitable mixtures thereof, and vegetable oils. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Suitable pharmaceutical agents for use with the excipients described herein would include any pharmaceutical agent that can form an association with the keratin formulations through non-covalent, covalent, or steric; interaction. These agents would include protein therapeutic agents, such as growth factors. In regard to oral administration, such agents may include compounds such as acetaminophen, tetracyclines, penicillins, vitamins, antacids, non-steroidal antiinflammatory agents, anesthetics, breath fresheners, and minerals, for example.

In those embodiments in which transdermal administration is desired, the disclosed compositions may be formulated to be administered by use of a skin patch, or transdermal delivery system. Transdermal administration may be accomplished by any of a number of systems known in the art. Examples of systems that may be adapted for use with the compositions described herein include those systems of transdermal administration described in U.S. Pat. No. 4,816, 252; U.S. Pat. No. 5,122,382; U.S. Pat. No. 5,198,223; U.S. Pat. No. 5,023,084; U.S. Pat. No. 4,906,169; U.S. Pat. No. 5,145,682; U.S. Pat. No. 4,624,665; U.S. Pat. No. 4,687,481; U.S. Pat. No. 4,834,978; and U.S. Pat. No. 4,810,499 (all incorporated herein by reference).

These methods typically include an adhesive matrix or drug reservoir system and may include a skin permeation enhancement agent such as ethanol, polyethylene glycol 200 dilaurate, isopropyl myristate, glycerol trioleate, linolenic acid saturated ethanol, glycerol monooleate, glycerol monolaurate, n-decyl alcohol, capric acid, and certain saturated and unsaturated fatty acids, and their esters, alcohols, monoglycerides, acetate, diethanolamides and N,N-dimethylamides (See for examples, U.S. Pat. No. 4,906, 169).

The release rate of an active agent from a keratin excipient preparation, when that active agent is not associated with the keratin excipient, is determined by the rate at which water is absorbed and the keratin solid disintegrates. The water absorption rate of the solid keratin can be controlled by the number of sulfonic acid residues generated in the oxidation procedure. By exposing the keratin source material to extremes of oxidant concentration, temperature, and time, extremes of absorption rate can be obtained. For example, at low oxidant concentration, colder temperatures and short time periods, relatively few disulfide residues will be converted to sulfonic acid residues. Such a keratin solid, further processed as described herein will absorb relatively little water and disintegrate relatively slowly. Conversely, a keratin solid prepared at high oxidant concentration, at boiling temperature for a long time period, further processed as described herein, will absorb relatively large amounts of water and disintegrate relatively quickly. Disintegration rates between these extremes can be obtained by processing the keratin source material using intermediate conditions. When the active agent is associated, such as ionically, with the keratin excipient, the release rate is determined by both the rate at which water is absorbed and the keratin solid disintegrates and the rate of dissassociation of the active agent from the keratin excipient. For some materials which are so tightly bound that release by dissassociation alone is ineffectual, degradation of the keratin solid must occur before the drug molecule can become dissolved in the surrounding media. The release rate under these conditions can be controlled by the degradation rate of the keratin solid. In general, oxidation and formulation conditions will effect the hydrolytic stability of the hydrogel containing the drug compound. Peracetic acid oxidized keratin provides a more hydrolytically stable gel than does hydrogen peroxide oxidized keratin, for example. Parameters such as oxidant, oxidation time and solids content of the hydrogel have been shown to be important parameters in controlling in-vitro stability at body temperature.

In some embodiments of the invention, a composition for the delivery of pharmaceutical agents is in the form of a nonwoven film comprising a synthetic polymer and a keratin material. The synthetic polymer may be, but is not limited to, α-olefins, acrylates, urethanes, acetates, nylons, esters, and copolymers thereof. In some embodiments the nonwoven composition is a laminate, which may be a tri-laminate comprising two outer layers of synthetic polymer and a middle layer of keratin material. The keratin material in the middle layer may be partially exposed by openings in the two outer nonwoven synthetic polymer layers. In some embodiments of the invention the synthetic polymer layers are nonwoven synthetic polymer webs. The nonwoven film pharmaceutical delivery composition may be used externally or internally.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments herein.

DETAILED DESCRIPTION OF THE INVENTION

Figure 1:
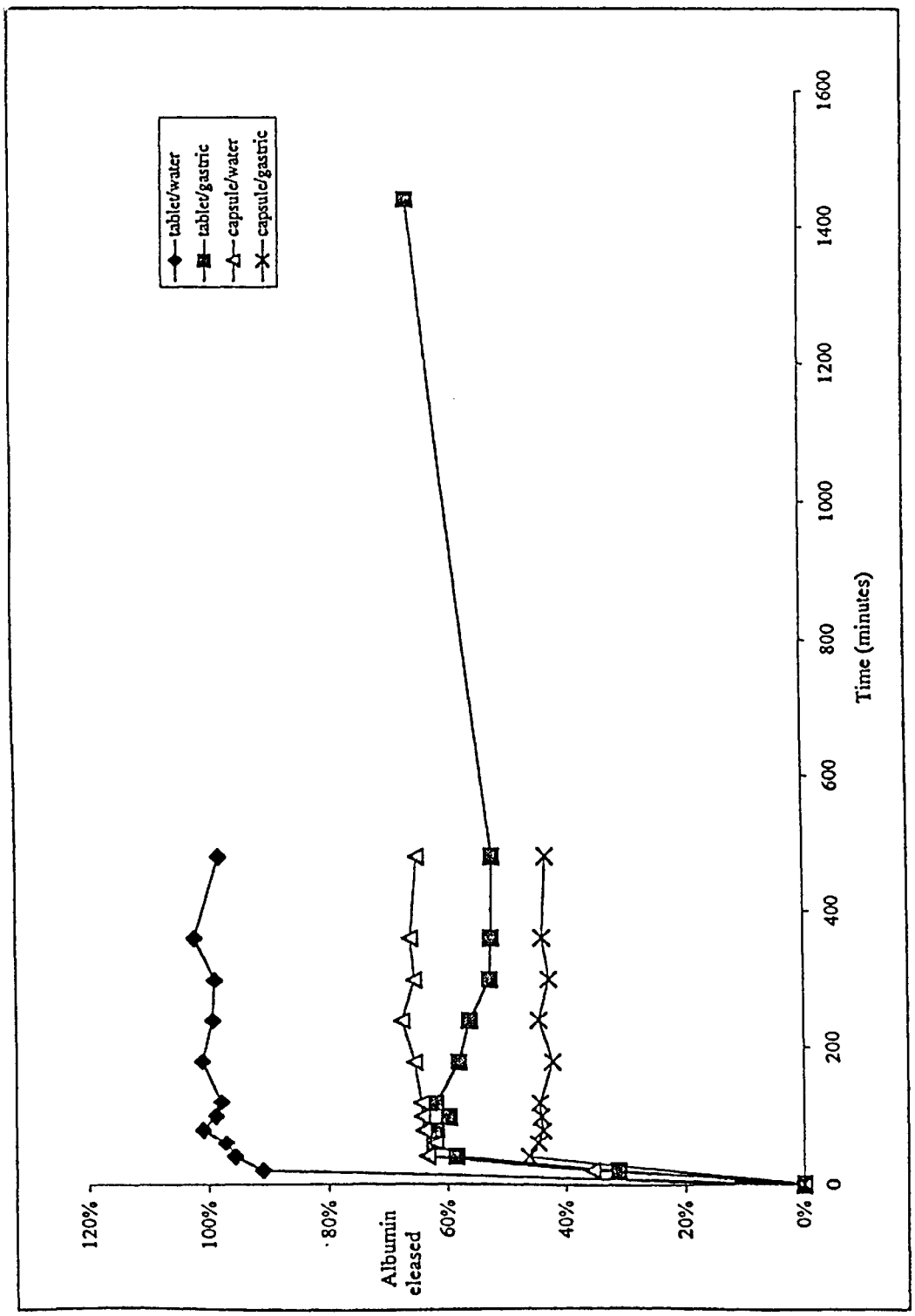
FIG. 1. Release of albumin from keratin tablets.

The present invention includes a hydratable solid derived from keratin that is highly absorbent and can form a hydrogel or viscoelastic hydrogel upon the application of water. The keratin solid can include protein having an ionizable pendant group such as sulfonic acid that can be derived from an oxidized protein disulfide linkage. A preferred source of protein is keratin, and particularly preferred is keratin obtained from hair, including human hair. While hair is a preferred source of keratinous material, other keratinous materials are also believed suitable for use in the present invention. Examples of other sources include animal hair, skin, hooves, feathers, beaks, feet and horns. The patient or a human donor are some preferred sources of hair, as hair from these sources is most likely to result in a non-immunogenic product, although animal hair may be acceptable for many individuals for many applications. In one method according to the present invention, hair is provided, preferably clean and unbleached. In another method, the hair is washed with Versa-Clean™ (Fisher Scientific, Pittsburgh, Pa.), rinsed with deionized water, and allowed to dry.

A. Preparation of Oxidized Keratin

The hair can be oxidized in peracetic acid or another suitable reagent such as $H_2O_2$. One method utilizes between about 1% to 32% peracetic acid, at a temperature between about 0 degrees C. and 100 degrees C. for between 0.5 and 24 hours. In one method, about 1 weight/volume percent peracetic acid is used. One method treats 30 grams of hair with 500 mL of 4% peracetic acid at 4 degrees C. for 24 hours. Another method treats the hair at room temperature for 24 hours. Yet another method treats the hair at about 90 degrees C. for about 10 hours. In a preferred method, the hair is treated by heating the hair in the oxidizing agent for between about 1 and 4 hours at a temperature between about 20 and 100 degrees C. In a more preferred method, the hair is treated by heating the hair in the oxidizing agent for between about 1 and 2 hours at a temperature between about 80 and 100 degrees C. In a most preferred method, the hair is treated by heating the hair in about 2 weight/volume percent oxidizing agent for about 2 hours at a temperature of about 100 degrees C. The oxidation is believed to cleave a significant portion of keratin disulfide bonds forming cysteic acid residues having sulfonic acid groups. The sulfonic acid groups are believed to be hydrophilic in nature and will ionically bond to cations later in the process, forming a salt of the keratin and cation. The partial oxidation is also believed by Applicants to release existing short chain peptides, or form additional short chain peptides, which can remain associated with, or entrained in the keratin structure.

After oxidation, the keratin solid can be recovered from the oxidizing liquid using filtration or other suitable methods such as centrifugation or decantation. The recovered, oxidized solid can be washed with water or alcohol such as methanol or ethanol to remove the excess oxidizing agent. In a preferred embodiment, washing is limited to avoid removing too much of any soluble peptide chains entrained in the keratin.

B. Preparation of Hydratable Keratin

The solid fraction can be suspended in a suitable solvent or solvent mixture. The solvent should be capable of at least suspending the hair or keratin solid and keeping the solid sufficiently swelled for subsequent reaction. The solvent is preferably a non-aqueous solvent, as the presence of water can act to hydrolyze peptide backbone bonds, which can result in an inferior product. The solvent should be able to solubilize the later added base. One group of suitable solvents includes alcohols such as methanol and ethanol. Other solvents such as ether, tetrahydrofuran (THF), acetone, propylene glycol, 1,4-dioxane and glycol ethers may also be suitable as solvents. Small amounts of water will assist in swelling the keratin and may therefore be added to the aforementioned solvents in an amount up to 20 volume percent. The solvent used is preferably volatile to promote evaporation from the final solid product.

The hair or keratin solvent suspension can then have the pH titrated upward to at least about pH 7. Increasing the pH deprotonates the sulfonic acid groups, leaving the sulfonic acids free to exchange with another cation. The pH can be adjusted with a base, preferably having a monovalent cation. Preferred bases include sodium hydroxide and potassium hydroxide.

The pH-adjusted keratin suspension can be heated for a time and temperature sufficient to swell the keratin structure and promote neutralizing of the sulfonic acid sites with the provided cation. In a preferred method, the keratin suspension is boiled between about 0.5 hours and 12 hours. More preferably, the keratin suspension is boiled between about 0.5 hours and 3 hours. In one method, the keratin suspension is boiled for about 1 hour. Boiling for too long a time period leads to a mushy keratin which results from degradation of the peptide backbone. A hydrated keratin product is less preferred due to the greater difficulty of grinding the keratin.

After boiling, the keratin is preferably allowed to continue to react with the provided base cation at lower temperature and with stirring. The lower temperature reaction preferably takes place at a temperature of between about 15 and 30 degrees C. for between about 1 and 24 hours. More preferably, the lower temperature reaction takes place at a temperature of between about 20 and 25 degrees C. for between about 1 and 5 hours. In one method, the keratin suspension is allowed to react with stirring at room temperature for about 5 hours. In certain embodiments the reaction is held at the boiling point of the solvent for about 2 hours.

After reacting at lower temperature, the reacted solid can be separated from the solvent using any suitable method such as filtration. The solid is preferably washed with a solvent such as the same solvent used in the reaction. Washing the keratin removes some of the base, which is preferably removed. The base is preferably removed to make the keratin solid less caustic.

After filtration and washing, the keratin can be dried by a method such as evaporation under vacuum. In one method, the keratin is dried at room temperature under about 5 mm Hg vacuum for about 2 hours. The dried keratin is preferably somewhat brittle, which can result in a better product after grinding. The dried keratin can be shredded into fibers and can further be ground into a powder. The dried keratin can be directly ground into a powder using a mortar and pestle, a ball mill, or other means of breaking down or comminuting the dried keratin into particles. Alternatively, the keratin can be ground or milled in the solvent used for said neutralization step.

One resulting hydratable fiber or powder has been observed to absorb about 10 to 13 times its own weight in water. In one test, fibers having a length of between one quarter and one-half inch were observed to absorb an average of 1300%+/-33% of their weight in water at a temperature of 21.5 degrees C. The fiber has been observed to absorb at least 10 times its own weight in water within about 10 seconds. The powder has been observed to rapidly absorb water as well.

The fibers were also tested for various toxicity parameters and were found to be non-toxic, non-irritating, non-sensitizing, and biocompatible as indicated in Table 1.

TABLE 1

Hydratable Keratin Toxicity Testing Data

| Test | Standard Protocol | Result |
| --- | --- | --- |
| Acute Oral Toxicity | Biological Evaluation of Medical Devices - Part 11: Tests for Systemic Toxicity; ISO 10993-11, 1993. | Non-toxic at 2 g/kg |
| Acute Dermal Toxicity | Biological Testing of Medical and Dental Materials and Devices - Part 10: Irritation and Sensitization Tests; ISO 10993-10, 1995. | Non-toxic at 2 g/kg |
| Acute Irritation | Biological Testing of Medical and Dental Materials and Devices - Part 10: Irritation and Sensitization Tests; ISO 10993-10, 1995. | Non-irritating at 33.3 wt. % |
| Kligman Sensitization | Biological Testing of Medical and Dental Materials and Devices - Part 10: Irritation and Sensitization Tests; ISO 10993-10, 1995. | Non-sensitizing at 33.3 wt. % |

TABLE 1-continued

Hydratable Keratin Toxicity Testing Data

| Test | Standard Protocol | Result |
| --- | --- | --- |
| Material Mediated Pyrogen Assay | Biological Evaluation of Medical Devices - Part 11: Tests for Systemic Toxicity; ISO 10993-11, 1993. | Passed |
| Systemic Injection | Biological Evaluation of Medical Devices - Part 11: Tests for Systemic Toxicity; ISO 10993-11, 1993. | Passed |
| Reverse Mutation Assay (Ames Test) | Biological Evaluation of Medical Devices - Part 3: Tests for Genotoxicity, Carcinogenicity, and Reproductive Toxicity, ISO 10993-3, 1992. | Passed |

C. Preparation of Nonwoven Films

1. Nonwoven Film Comprising Hydratable Keratin Fibers

Hydratable keratin fibers may be incorporated into a nonwoven film by admixing with synthetic fibers which serve as a binder. Such a nonwoven film can be formed by mixing synthetic fibers made from, but not limited to, α-olefins, acrylates, urethanes, acetates, nylons esters, or copolymers thereof with water-absorbent keratin fibers and heat pressing the mixture into a film of desired thickness. The synthetic fibers will serve as a binder for the keratin fibers, while not completely encapsulating them. This morphology provides mechanical integrity to the film, while allowing the keratin fibers to absorb water. The hydrated fibers can also release material which has been shown to be beneficial for repairing damaged epithelial tissue.

Nonwoven films can be prepared by preparing nonwoven webs of a synthetic polymer and then placing a layer of hydratable keratin fibers between two layers of the nonwoven polymer-web. For example, a nonwoven film was produced by first preparing a nonwoven web measuring approximately one half inch thick by 24 inches wide using 9 denier, 38 mm length polypropylene fibers. The web was made using a Rando-Webber, (Fiber Controls, Inc. Gastonia, N.C.) air laying machine operating at 2000 rpm, 12 ft./minute let off speed with a feed rate of 4 ft./minute. A web of approximately 20 feet in length was coated over half of its length on one side with keratin fibers of approximately 2–5 mm in length. The keratin was spread on the web using a hand sifter. The uncoated section of the web was folded back over the coated section to form a laminate of keratin between two layers of polypropylene. The laminate was passed through a Sigrna heated roller press (BF Perkins, Rochester N.Y.). The rolls were oil heated to 160° C. and a pressure of 350 pounds per linear inch was applied. The surface of the top roller was textured so as to impress a texture in the finished nonwoven film. The laminate was fed through the rollers at approximately 4 ft./minute and the polypropylene softened and pressed such that a film of approximately 3 mm in thickness resulted. This nonwoven film was bound together by the polypropylene, but retained some flexibility. The keratin fibers were at least partially exposed such that the film wetted easily and the keratin became gelatinous upon addition of water.

Nonwoven films can be made by other procedures. For example, if a more open nonwoven is desired, a laminate of keratin and synthetic fibers can be prepared as described above, and this laminate processed by a through air dryer. The through air dryer is capable of heating the laminate but does not apply pressure to the film. In this process, the synthetic fibers can be softened and bound together, thus providing a structural matrix for the keratin fibers. The result is a nonwoven web which retains more of its original, open morphology. Also, films made with synthetic fibers can sometimes be stiff. The example given above resulted in a film resembling burlap. If a softer film is desired, alternative fibers or blends of fibers may be used to produce the nonwoven web. A blend of cotton and polypropylene, for example, would provide a softer, more pliable nonwoven film. Cotton fibers can conveniently be blended into the nonwoven web during the air laying or carding process, prior to coating with keratin fibers. Other natural fibers such as hemp may also be used.

These nonwoven films are produced from a loose, laminated precursor. However, the keratin fibers are exposed to the surface in the final product. Although the exemplified polymeric binder is hydrophobic, the nonwoven film wets easily and readily absorbs water. Once water is applied to the film, the keratin fibers absorb it and swell, thus forming a hydrogel which is entrained in the unswollen binder. This type of film is of utility as a wound dressing because of the capability of absorbing wound exudate and forming a hydrated, gelatinous cover over the wound site. Such a dressing provides a closed, moist environment, conducive to wound healing. Drug actives that are useful in wound healing applications such as antibiotics, anti-inflammatory agents, analgesics and the like may also be bound to the keratin used in producing the nonwoven films. The nonwoven film may be produced using a biocompatible synthetic binder material such as polylactic acid, polyglycolic acid, copolymers thereof, and drug loaded keratin. Such a nonwoven device is useful as a biocompatible implant for controlled and/or sustained delivery of active agents. Due to the water absorbency, these nonwoven films also have utility as components of disposable diapers, feminine hygiene products as well as any other application where a nontoxic film with biocompatibility and absorbency is desired and the healing of damaged skin or other epithelial tissue is deemed beneficial or necessary. These films also have utility as implant materials for the repair of damaged hard or soft tissues, as cell scaffolds and tissue engineering applications.

2. Nonwoven Film Comprising Oxidized Hydratable Keratin Powder

Nonwoven films can also be prepared with oxidized keratin powder. For example, a nonwoven web measuring approximately one half inch thick by 24 inches wide was prepared using 1.7 denier, 38 mm length Fortrel® polyester fibers supplied from Wellman, Inc. (Johnsonville, S.C.). A blend of 20 wt. % low melt and 80 wt. % high melt fibers was first mixed by hand, then run through a Garnett fine opener, and finally carded. This was done prior to laying the web to provide a homogeneous sample. The web was made using a Rando-Webber (Fiber Controls, Inc, Gastonia, N.C.)

air laying machine operating at 2000 rpm, 12 ft./minute let off speed with a feed rate of 4 ft./minute.

The web was mechanically entangled using a hydrobonder from Honeycomb Systems, Div. (Division of Valmet, Inc., Biddeford, Me.). This equipment consists of a screen conveyor and a manifold of high pressure waterjets. The web passes under the water jet manifold and the force of the water forces the fibers through the screen, thereby entangling them. The degree of entanglement can be controlled by the mesh size of the screen conveyor. The excess water was removed using a vacuum stripper manufactured by Evac Corporation, (Spartanburg, S.C.). This process reduced the web's thickness to approximately one eighth inch and resulted in a more tightly entangled web with more structural integrity than one produced using only the air laying technique.

Two rolls of web, 20 feet in length, were prepared using this process and used to make a laminate with hydratable keratin powder. The keratin powder was less than 300 μm in size and was prepared as described for keratin fibers. The laminate was prepared by conveying the two webs from separate spools and spraying the powder onto the bottom web. Powder was sprayed using a GEMA™ powder sprayer with an electrostatic spray gun (the electrostatic feature was not used). The gun was operated at 2 psi with a flow of 4.5 $m^3$/hour through the reservoir and a make-up flow of 1.5 $m^3$/hour through the gun. The nonwoven laminate was conveyed with a take-up winder operating at 32 ft./minute. The use of a tighter web allowed small keratin particles (length of less than 1 mm) to be used without significant loss. This was especially important during the winding and unwinding operations prior to thermal bonding. The web could also be moistened slightly prior to spraying the keratin in order to promote adhesion.

The nonwoven laminate was passed through a Sigma heated roller press. The rolls were oil heated to 160° C. and a pressure of 200 to 215 pounds per linear inch was applied. The surface of the top roller was textured so as to impress a texture in the finished nonwoven film. The laminate was fed through the rollers at approximately 15 to 17 ft./minute. This procedure resulted in a nonwoven film of approximately 3 mm in thickness. The surface of the film was smoother than the film described previously and the use of polyester, rather than polypropylene, produced a softer, more pliable film. The keratin powder was at least partially exposed such that the film wetted easily and the keratin became gelatinous upon addition of water.

D. Keratin Delivery Systems

Active agents can be incorporated into a hydratable keratin excipient to form a delivery system. By "active agent" is meant a compound, the delivery of which is the object of the application of the preparation comprising that compound and the keratin excipient of the present invention. Delivery of an active agent is generally desired because of a beneficial and/or desired effect or attribute imparted by the agent upon delivery. Physical classes of active agents that can be incorporated into the keratin excipient of the present invention include, but are not limited to, compounds that may ion exchange with sulfonic acid groups, those compounds that may otherwise be formulated as hydrochlorides, compounds that form an electrostatic association with the keratin excipient, polar agents, polynucleotide agents, and polypeptide and peptide agents. Polypeptide agents include both recombinant and native polypeptides. For example, insulin is a polypeptide agent that may be incorporated into the keratin excipient of the present invention. Polar compounds include, but are not limited to 4-acetaminophenol, aspirin and beta-lactams. Compounds that may otherwise be formulated as hydrochlorides include, but are not limited to phenylpropanolamine and pseudoephedrine.

The active agent may be a pharmaceutical agent. By "pharmaceutically active agent" is meant any compound commonly referred to as a "drug" and its equivalents which include any physiologically or pharmacologically active substance that produces a localized or systemic effect or effects in animals. The term "animal" includes mammals, humans and primates such as domestic, household, sport or farm animals such as sheep, goats, cattle, horses and pigs, laboratory animals such as mice, rats and guinea pigs, fishes, avians, reptiles and zoo animals. Examples of pharmaceutical agents that may be formulated as hydrochlorides, and examples of pharmaceutical agents in general, are found in Remington: The Science and Practice of Pharmacy, (19th ed., ed. A. Gennaro) 1995, The Pharmacological Basis of Therapeutics, by Goodman and Gilman, 6th Ed., 1980, published by the MacMillan Company, London and in The Merck Index, 11th Edition, 1989, published by Merck & Co., Rahway, N.J., herein incorporated by reference in their entirety. A non-exhaustive list that exemplifies some of the classes and types of pharmaceutical agents that may be used in the present invention is provided in Table 2.

TABLE 2

| | |
|---|---|
| Analgesics | aspirin, acetaminophen, morphine, oxymorphone, codeine, oxycodone |
| Antianxiety Drugs | buspirone, benzodiazepine, venlafaxine |
| Antiarrhythmics | flecainide, encainide, lidocaine, digoxin, beta-blockers, procainamide |
| Antibacterials | beta-lactams, aminoglycosides, macrolides, clindamycin, tetracylin, quinolones, sulfonamides, trimethoprim-sulfamethoxazole, sulfisoxaole, sulfasalazine, |
| Antibiotics | penicillins cephalosporins, amnioglycosidases, macrolides, fluroquinolones, chloamphenicol, rifampin, vancomycin |
| Anticonvulsants | phenytoin, ethosuximide, valproate, diazepam |
| Antifungals | amphotericin B, clotrimaozole, econazole, fluconazole, flucytosine, griseofulvin, haloprogrin, ketoconazole, itraconazole, miconazole, nystatin, tolfanate, undecylenic acid, terconazole, triacetin |
| Antihistamines | alkylamines, ethanolamines, ethylenediamines, piperazines, phenothiazines, piperidines |
| Anti-Inflammatories | betamethasone dipropionate, clobetasol propianate, amcinonide, halcinonide, fluocinolone acetonide, betamethasone alerte, flubiprofen, ibuprofen, indomethacin, ketoprofen, mefenamic, naproxen, phenylbutazone, suldinac |

TABLE 2-continued

| | |
|---|---|
| Antivirals | acyclovir, amantidine, didanosine, inosiplex, intrathecal, ribavirin, ganciclovir, triflurdine |
| Cytotoxics | prednisolone, azathioprine, cyclophosphamide, cyclosporine, tacrolimus |
| Cytokines | inteferon alpha, interferon beta, colony stimulating factors (GM-CSF, M-CSF, G-CSF), interleukins 1 through 11, tumor necrosis factor beta |
| Growth Factors | platelet-derived growth factor, epidermal growth factor, fibroblast growth factor, insulin-like growth factors, transforming growth factor beta |
| Muscle Relaxants | benzodiazepines, imidazopyridine, diphenhydramine, pyrilamine |
| Sympathomimetics | phenylpropanolomine, phenylephrine, psudoephedrine |
| Vitamins | A, $B_6$, $B_{12}$, C, D, B, folacin, thaimin, riboflavin, niacin, pantothenic acid, biotin |

The active agent may be a cosmetic agent. The term "cosmetic" used in relation to a formulation or product means a formulation or product that qualifies as a cosmetic under the Federal Food, Drug and Cosmetic Act, 21 U.S.C. §321(i). By "cosmetic agent" is meant an agent that is incorporated in a cosmetic formulation or product and that agent is reported or believed to impart a beneficial and/or desirable effect or attribute upon application of the cosmetic. Cosmetic agents include, but are not limited to, anti-wrinkle agents, such as retinol and alpha-hydroxy acids, polypeptide and peptide agents derived from skin proteins (e.g., keratin, collagen and elastin), sunscreens, humectants, antioxidants, vitamins, tanning agents (both artificial and those that effect melanogensis), and whitening agents. Descriptions of cosmetic agents may be found in International Cosmetic Ingredient Dictionary and Handbook, Cosmetic Toiletries and Fragrance Association, $8^{th}$ ed. 2000, and A Consumers Dictionary of Cosmetic Ingredients, Ruth Winter, Three Rivers Printers, $5^{th}$ ed, 1999, both herein incorporated by reference.

In some embodiments of the present invention, the keratin excipient may be incorporated in a nonwoven film. In other embodiments of the present invention, the keratin excipient may be incorporated into a drug delivery device. Examples of systems that may be adapted for transdermal use with the compositions described herein described in U.S. Pat. No. 4,816,252; U.S. Pat. No. 5,122,382; U.S. Pat. No. 5,198,223; U.S. Pat. No. 5,023,084; U.S. Pat. No. 4,906,169; U.S. Pat. No. 5,145,682; U.S. Pat. No. 4,624,665; U.S. Pat. No. 4,687,481; U.S. Pat. No. 4,834,978; and U.S. Pat. No. 4,810,499 (all incorporated herein by reference). Examples of systems that may be adapted for inhalation of the compositions described herein are described in U.S. Pat. No. 5,884,620 and U.S. Pat. No. 5,960,792, both incorporated herein by reference.

In some embodiments, the basis of drug delivery is binding an active agent in a keratin matrix for later release by some mechanical, chemical, biochemical or cellular mechanism. Active agents can either be electrostatically bound or physically entrained in the matrix. Electrostatic binding can occur in the form of ionic bond formation (specific, results in tightly bound active agent) and Van der Waal's bond formation (less specific, results in a less tightly bound drug). Entraining an active agent can be most effectively accomplished by providing a processes that incorporates intimate mixing of the agent and the matrix, most notably, solution processing. Multiple combinations of these binding mechanisms are possible, depending on the structure and functionality of the drug molecule.

Electrostatic binding (ionic and Van der Waal's) can be accomplished by performing an ion exchange with oxidized keratin in nonaqueous media. The media needs to solubilize the drug and effectively suspend, and at least slightly swell the keratin. Ionic bonds will form between ionic species, whereas Van der Waal's bonds will form between ionizable functional groups of opposite partial charge.

Entrainment can be accomplished by physical mixing of the active agent and the keratin matrix. The more intimate the mixing, the more likely to result in tightly bound drug. This approach works best for large molecules such as protein therapeutics because larger molecules can entangle more effectively than smaller ones. A most effective approach to promote intimate mixing is to add an active agent and keratin matrix in suspension or solution. This can be accomplished by adding an aqueous solution of active agent to dehydrated keratin absorbent and forming a hydrogel, by adding a keratin hydrogel to dehydrated active agent, or by adding a solution of active agent to a keratin hydrogel. The resulting drug loaded hydrogel can be processed into a dosage for in the gel state or dried and ground into a powder.

The keratin matrix needs to be of a particle size category in dosage forms to be used for inhalation or intravenous (IV) injection. Dry, solid keratin loaded with an active agent as described previously can be processed into a powder of specific particle size using any one of a variety of grinding techniques known to those skilled in the art such as grinding or milling. Classification into a specific particle size range can be performed by sieving. For inhalation applications, particulates of different sizes will reach specific areas of the respiratory system. For example, particles that are greater than 5 microns will reach the nasopharynx. Particles between about 2 and about 5 microns will reach the trachea and bronchus. To reach the alveoli, particles must typically be less than about 1 micron. It has been shown that particles of about 3 microns or larger are deposited in the respiratory tree and become encysted. Keratin particles for drug delivery must reach the alveoli in order to be efficiently absorbed by the bloodstream and therefore must be less than about 1 micron.

For intravenous injections applications, the drug loaded keratin particles need to be small enough to be metabolized in the bloodstream (i.e. absorbed by cells) and also sufficiently small enough so as not to cause blockage of the small capillaries in the circulatory system. The limiting size in this regard is the lesser of the two, namely the mean capillary diameter (in humans, ca. 5 microns).

For both the inhalation and intravenous injection dosage forms, the particles sizes discussed must be the fully hydrated particle size. Depending on the processing parameters of the keratin used and the conditions under which the drug is incorporated into the keratin matrix, hydration capacities will vary. Considering a maximum absorption mass of ca. 20 times, the maximum particle sizes discussed previously would be reduced by ca. 20 times. Specific swelling volumes would depend on the materials used since resulting densities will vary.

In various embodiments, the particle size is less than 0.5 micron, or less than 1.0 micron, or less than 2 microns, or less than 3 microns, or less than 4 microns, or less than 5 microns, or less than 10 microns, or less than 20 microns, or less than 30 microns, or less than 40 microns, or less than 50 microns, or less than 100 microns. In other embodiments the particle size is between about 0.1 micron and about 1 micron, or between about 0.1 micron and about 2 microns, or between about 0.1 micron and about 3 microns, or between about 1 micron and about 3 microns, or between about 1 micron and about 5 microns, or between about 1 micron and about 10 microns.

The active agent delivery system of the present invention offers distinct advantages over conventional drug dosage forms. As with most delivery systems, sustained or controlled release allows the level of an agent to be maintained at a more consistent concentration, thereby allowing larger doses to be administered on a less frequent basis. In the system described here, the chemical and material properties of the keratin determine the properties of the dosage form. For example, loading can be varied by the availability of sulfonic acid binding sites, which can in turn be controlled by the keratin oxidation process. Further, the disintegration and breakdown of the keratin can also be controlled by the relative amount of disulfide crosslinks remaining after the oxidation process. Disintegration and dissolution will effect the release kinetics of the dosage form. For longer term release applications, the release rate can be controlled by the hydrolysis rate of the keratin, which in turn can be controlled by processing and formulation parameters such as oxidant type, oxidation time, and solids content. When incorporated into a nonwoven wound dressing, the bound drugs can be tailored to those most beneficial to wound healing such as, for example, antibiotics, biocides, pain medications and growth factors.

Following are examples of preparation, testing and formulation of keratin delivery systems:

1. Dissolution Testing (a) Rotating Paddle Method

Dissolution tests are performed according to the standard United States Pharmacopoeia (USP) rotating paddle method. In this method, the volume of the dissolution medium is fixed and agitation is provided under defined conditions by the stainless steel paddle. A 1L volume of purified water or simulated gastric fluid (Lot. No. 76H9312, Sigma-Aldrich, St. Louis, Mo.) was used at 37° C.±0.5° C. The temperature of the dissolution medium was maintained at 37° C. by immersing the dissolution flask in a water bath. A cover was used on the system to avoid water loss through evaporation. After the temperature equilibrated, the samples were allowed to sink to the bottom of the vessel before rotation of the paddle. Rotation speed was kept constant at 50 rpm.

During the test, small volumes of sample were withdrawn at various time points, for example, every 20 minutes within the first hour (including a 0 time point) and every hour after that for 8 hours. Samples were taken from a precise point in the dissolution flask, halfway between the surface of the dissolution medium and the top of the rotating paddle, and not less than 10 mm from the wall of the vessel. The volume withdrawn during sampling was replaced with an equal volume of media, pre-warmed to 37° C. High-performance liquid chromatography (HPLC) was performed on the samples and the amount released from the dosage form calculated based on a calibration curve generated from solutions with known concentrations of the compound of interest.

(b) Franz Diffusion Cell

An alternative dissolution test for membranous or film topical formulations is by use of one-chambered Franz type diffusion cells (Franz, 1978). Franz cells may be obtained from Crown Glass (Somerville N.J.). In these cells, one side of a membrane is in contact with an aqueous solution and the other side is open to the ambient atmosphere, unless placed within a controlled atmosphere. The keratin-containing film or membrane is mounted in the diffusion cell such that one side is in direct contact with the aqueous receptor solution (Lee et al., 1986). The aqueous solution is continuously stirred and kept at 32° C. by means of a waterjacket.

Samples are removed from the aqueous medium by means of the sampling port at appropriate times. For example, samples may be taken every 20 minutes within the first hour (including a zero time point) and every hour after that for 8 hours. An additional sample may be taken at 24 hours. High-performance liquid chromatography (HPLC) or other suitable analytical quantification is performed on the samples and the amount released from the dosage form is calculated based on a calibration curve generated from solutions of known concentrations.

2. Albumin Containing Preparations

Samples containing albumin were made in tablet and capsule forms. Tablets were prepared by co-grinding a mixture of 80/20 dry keratin absorbent powder/bovine albumin. The keratin absorbent powder was prepared as described in Section VI. B supra, and the albumin was purchased from Sigma Chemical Co., St. Louis, Mo. (Lot No. 69H1257, Fraction V, 96% purity). The solid mixture was further homogenized by shaking in a closed container. Samples of 500 mg of the powder mixture were made into tablets using a pellet press at 30,000 psi (400 mg keratin, 100 mg albumin). The dissolution profile of these tablets was measured by the rotating paddle method.

Albumin capsules were prepared by dissolving 2 g of albumin in 200 g of deionized water. The albumin solution was added to 8 g of absorbent keratin powder to form a hydrogel. The hydrogel was thoroughly mixed and poured into petri dishes. The water was removed under vacuum at room temperature. After drying for approximately 36 hours, the resulting solid was ground using a mortar and pestle. 400 mg of the ground keratin/albumin powder (320 mg keratin/ 80 mg albumin) was placed into each of several two-part gelatin capsules (No. 0, Eli Lilly and Co., Indianapolis, Ind.). The dissolution profile of these tablets was measured using the rotating paddle method.

The results of the dissolution testing are summarized in the graph in FIG. 1. When the albumin was mechanically mixed with absorbent keratin in powder form (i.e. tablets), the disintegration and release were almost immediate and complete in water. Release from the tablet in gastric fluid was also immediate, although the equilibrium amount of albumin was significantly lower, suggesting that some of the albumin remained bound to the keratin. This is presumably due to a pH effect on either the keratin or the solubility or stability of the albumin in gastric fluid. An identical trend is evident in the data obtained from capsules.

Comparison of the tablet and capsule data reveals the effect of the different preparation procedures that were employed. In the case of the tablets, simple mechanical mixing resulted in more material ultimately being released, particularly in purified water, because mechanical mixing does not result in a high degree of interaction at the molecular level. When intimate mixing was employed, as in the case of the gelatin capsules, much less material was released over an equivalent time period. The intimate mixing was the result of first forming a gel from an albumin solution and keratin. In the hydrated state, albumin and keratin molecules are more free to interact on a molecular level. While not being bound to any theory, it is expected that intimate mixing would result in more tightly bound albumin and consequently, less release than a system employing less intimate mixing. The unreleased material will be available however, and would be dissolved as the keratin degrades in a biological system.

3. Phenylpropanolamine (Norephedrine) Preparations

Figure 2:
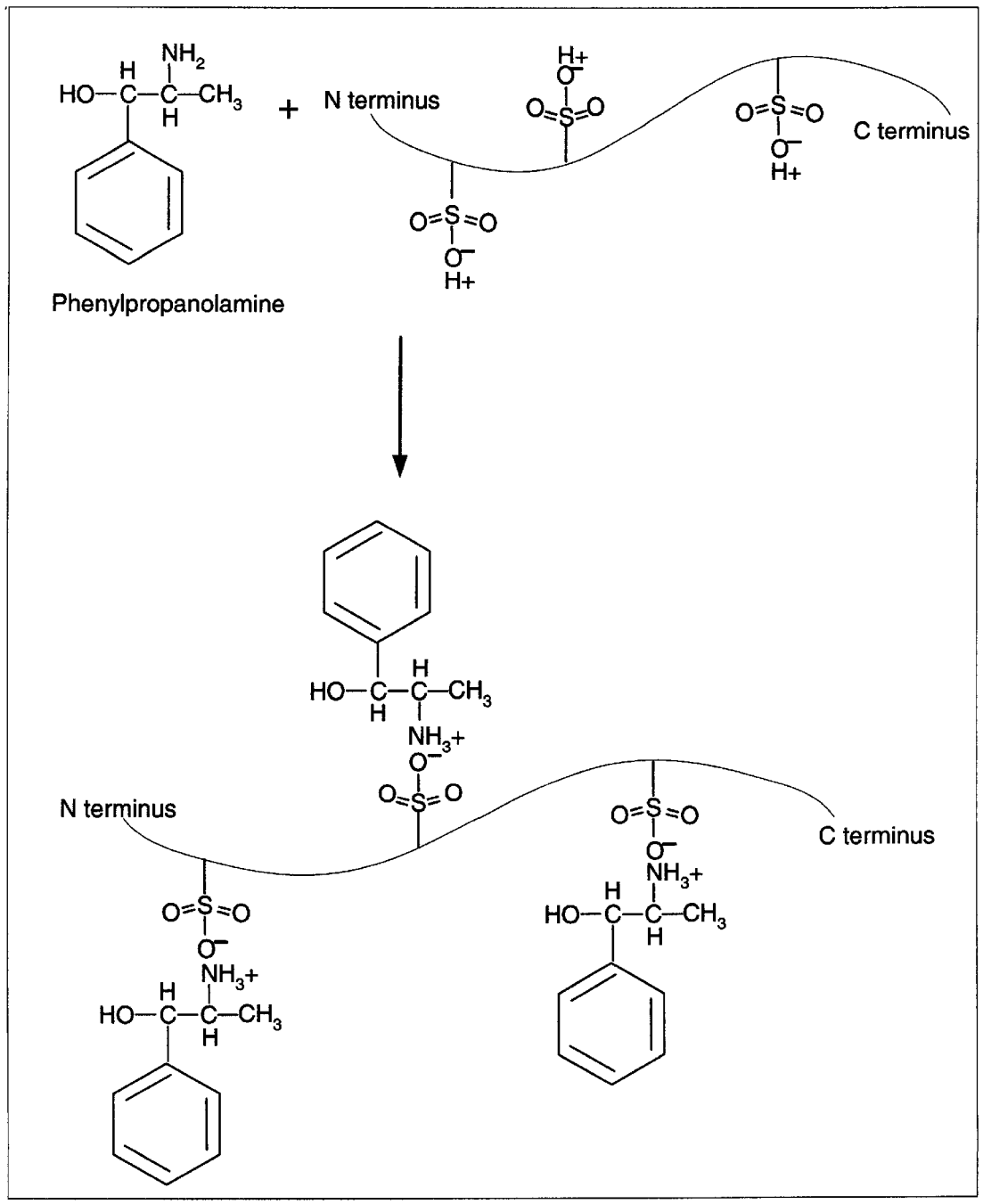
FIG. 2. Schematic of proposed mechanism for amine drug binding to oxidized keratin.

Tablet samples that incorporated the vasoconstrictor norephedrine were prepared by binding the drug to oxidized keratin in an ion exchange step. Six different oxidized keratin samples were prepared by boiling 30 g each of human hair in 500 mL of 2 w/v % $H_2O_2$ for 1, 2, 3, 4, 5 and 6 hours. Longer oxidation times results in the generation of more sulfonic acid residues. More sulfonic acid residues results in increased binding affinity which in turn results in increased drug loading capabilities for molecules that bind with sulfonic acid residues. Each of the oxidized keratin samples were ion exchanged with norephedrine by the proposed mechanism shown in FIG. 2. This was accomplished by dissolving a measured amount of norephedrine into ethanol, adding 5 g of oxidized keratin and heating to reflux for 2 hours, followed by stirring at room temperature for 24 hours.

Equivalents of norephedrine bound to the keratin were determined based on the equivalents of sulfonic acid generated during the oxidation process. For example, 5 g of hair oxidized for 4 hours would be exchanged with approximately $5 \times 10^{-3}$ moles of norephedrine. This calculation is based on data generated for a pH 7 titration curve for $H_2O_2$ oxidized hair which is shown in FIG. 3.

After binding the norephedrine in the ion exchange step, the solid keratin was separated by filtration, dried, ground and pressed into 500 mg tablets as described previously. The dissolution profile of these tablets was measured using the rotating paddle method.

Figure 3:
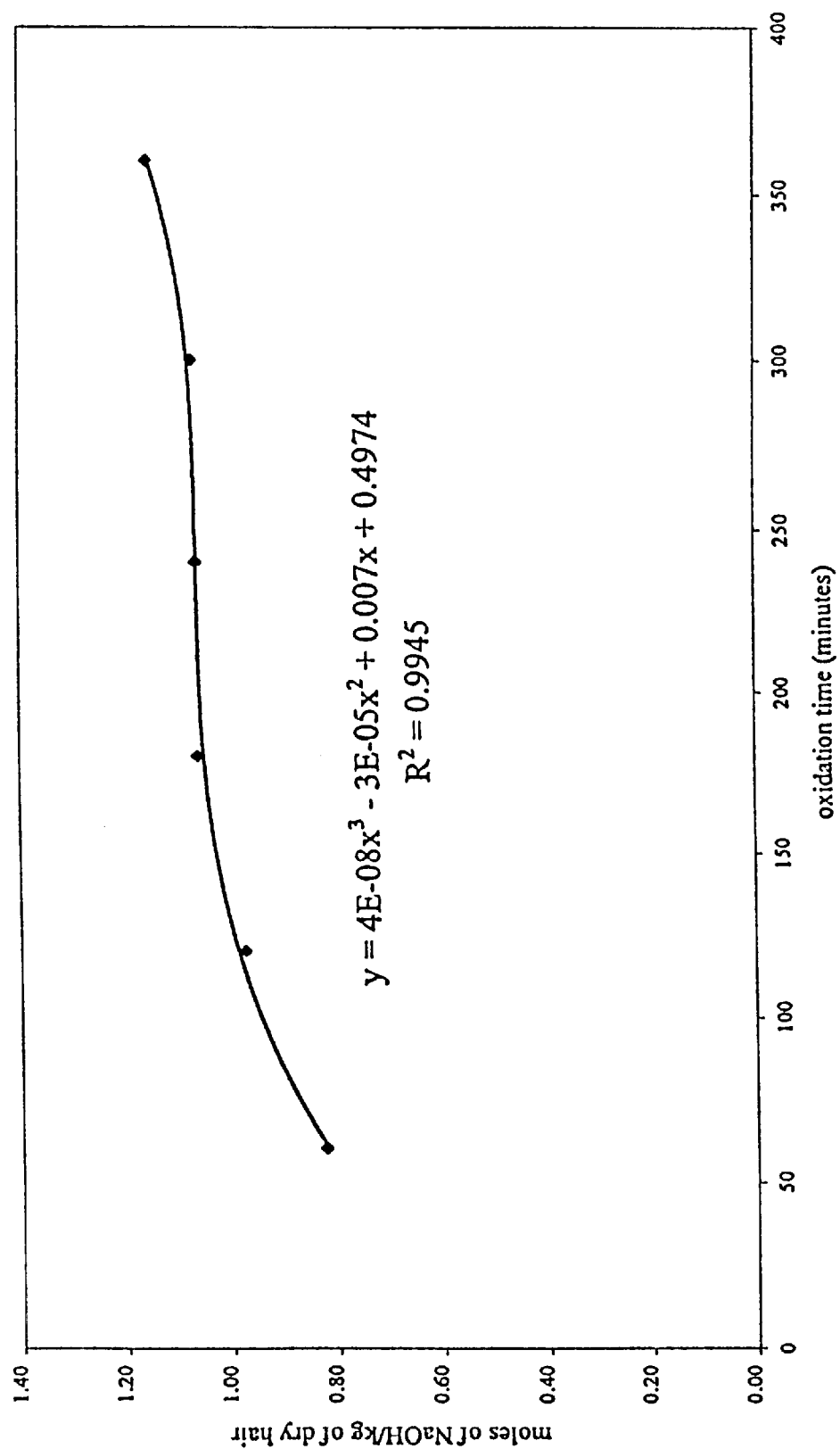
FIG. 3. Hydrogen peroxide oxidized hair pH 7 titration curve.
Figure 4:
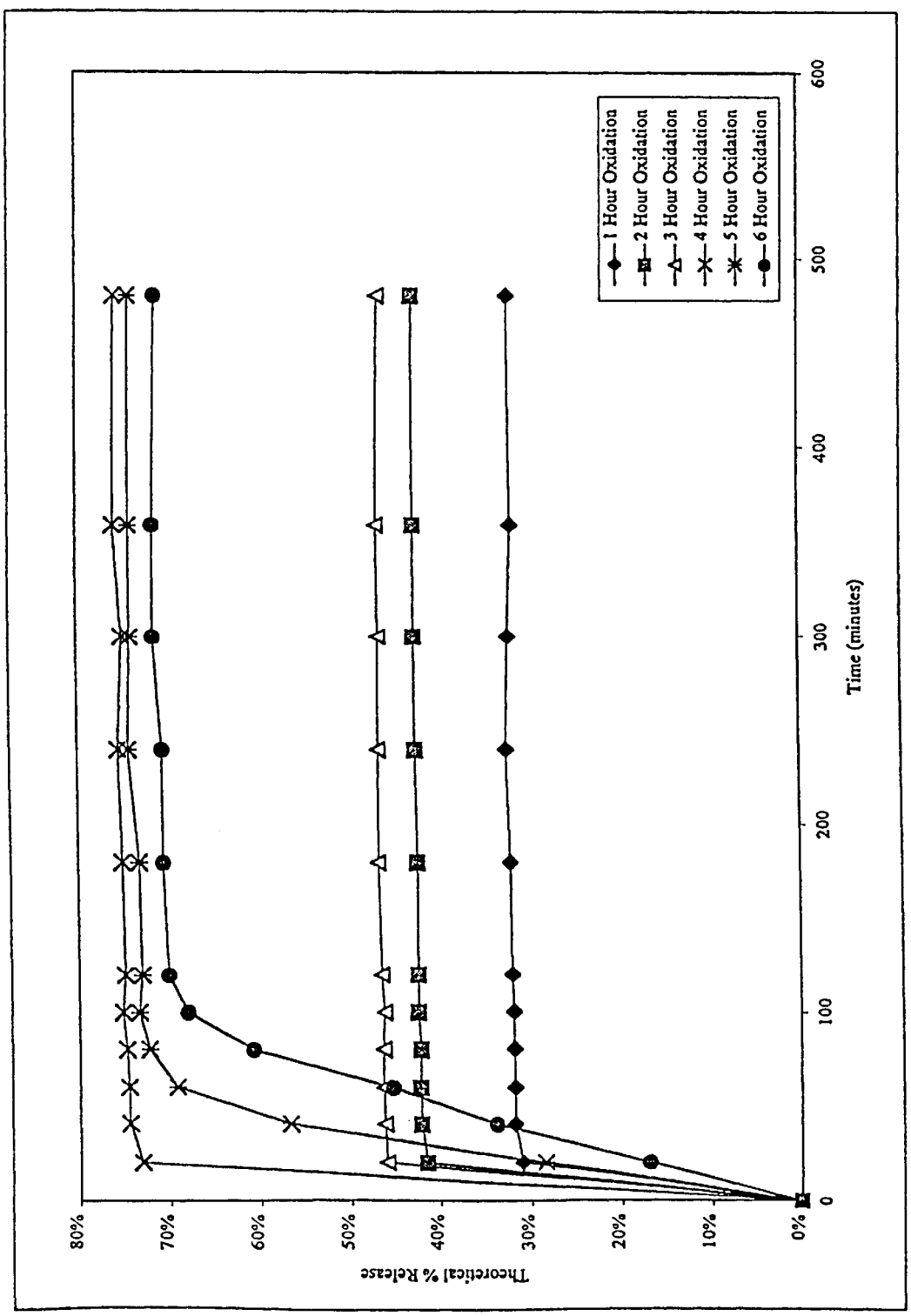
FIG. 4. Release of norephedrine from keratin tablets in simulated gastric fluid.

These data, displayed in FIG. 4, show a general trend toward higher drug loading at longer oxidation times, which is also suggested by the titration curve shown in FIG. 3. As discussed previously, longer oxidation times results in increased sulfonic acid residues, which in turn increases drug loading for molecules like norephedrine. In addition, longer oxidation times resulted in longer sustained release as demonstrated by the 5 hour and 6 hour oxidation samples. This is a kinetic effected based on the fact that longer oxidation times result in more sulfonic acid residues, more keratin surface area after the solid has been ground prior to the ion exchange process, and more efficient ion exchange due to greater diffusion. All of these factors serve to increase binding in more highly oxidized keratin.

Many drugs of interest are ionized at physiological pH. These drugs exist as a cation, anion or zwitterion (both cation and anion). These drugs require a counterion (with the exception of a zwitterion) with an opposite charge of equal magnitude. Since proteins contain both anionic (carboxylate, imidizole and, in the case of oxidized keratin, sulfonic acid) and cationic (amine and guanidyl) functionalities at physiological pH, drugs capable of forming a complimentary counterion to these functionalities will exhibit binding affinity.

The degree of binding may be estimated from the pKa of the drug of interest and the pH of the keratin protein in solution. The estimate is calculated by determining the pKa of the drug in its normal physiological form. If there is a substantial difference (>1) in the pKa of the drug versus the pH of the keratin, there is a possibility of binding. For example, drugs that contain amine functionalities are in the protonated form at physiological pH. The pKa of a protonated amine usually ranges from 9 to 10. Thus a protein that is acidic in aqueous solution will readily protonate a drug containing an amine forming a stable ammonium compound. Keratin absorbent produces a pH of 3.0 to 4 in aqueous solution. The binding in this case is ionic arising from the acid-base interaction of the protein and the drug. The number of binding sites can be garnered from the number of acid equivalents in the protein which in turn can be determined by titration.

4. 4-Acetaminophenol (Acetaminophen) Preparations

Samples that incorporated the antipyretic acetaminophen were prepared by binding the drug to oxidized keratin in an ion exchange step. Six different oxidized keratin samples were prepared by boiling 30 g each of human hair in 500 mL of 2 w/v % $H_2O_2$ for 1, 2, 3, 4, 5 and 6 hours. This was done in order to generate samples with different amounts of sulfonic acid residues, hence, different binding affinities and presumably, different release characteristics. Compounds with weak ability to form amine salts, such as acetaminophen, are expected to form acid-base interactions with the keratin molecules. Acetaminophen molecules also contain a phenolic functionality, which can participate in binding through Van der Waal's interactions. These binding mechanisms are similar to the ion exchange process described for norephedrine, but result in a less tightly bound drug. This binding was accomplished by dissolving a measured amount of acetaminophen into ethanol, adding 5 g of oxidized keratin and heating to reflux for 2 hours, followed by stirring at room temperature for 24 hours. Acetaminophen binding is most likely dominated by Van der Waal's interactions. pH is important only in so far as it effects the kinetics of the process. A sufficiently open tertiary structure for the keratin is important in the ionic exchange simply to promote interactions between molecules. The openness of the keratin is dependant on the oxidation so, indirectly, pH is important in Van der Waal's binding. Measured amounts of acetaminophen were estimated based on the amount of time the hair had been oxidized. The pH 7 titration curve for $H_2O_2$ oxidized hair that is shown in FIG. 3 was used as a guide for the loading of keratin with acetaminophen.

After binding the acetaminophen in the ion exchange step, the solid keratin was separated by filtration, dried, ground and pressed into 500 mg tablets as described previously. The dissolution profile of these tablets was measured using the rotating paddle method.

Evaluation of the loading of acetaminophen was accomplished by disintegrating a single tablet into a known volume of water over a one week period at room temperature. In addition, that samples were sonicated for 90 minutes prior to sampling. A sample of the solution was withdrawn and analyzed by HPLC.

Figure 5:
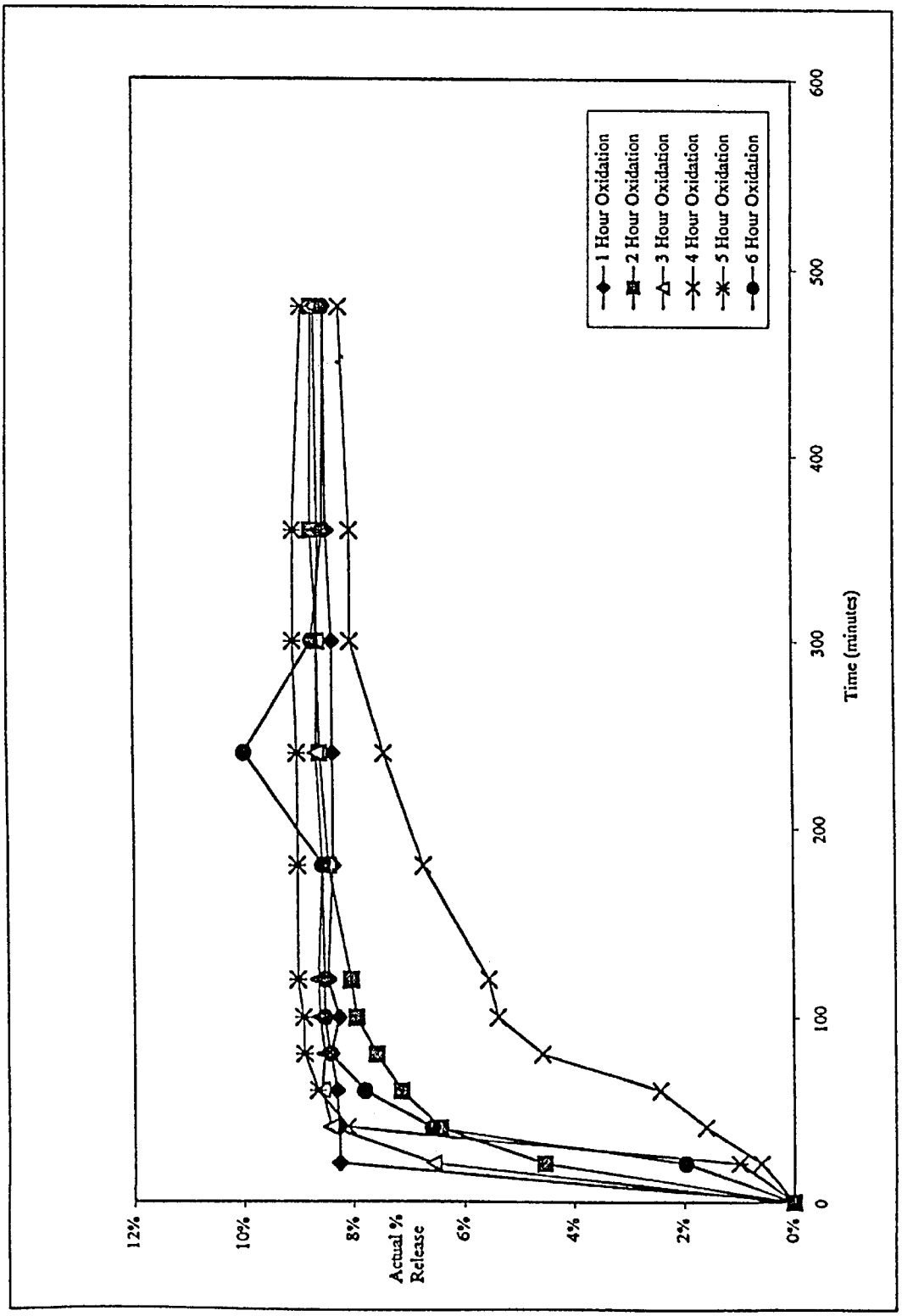
FIG. 5. Release of acetaminophen from keratin tablets in simulated gastric fluid.
Figure 6:
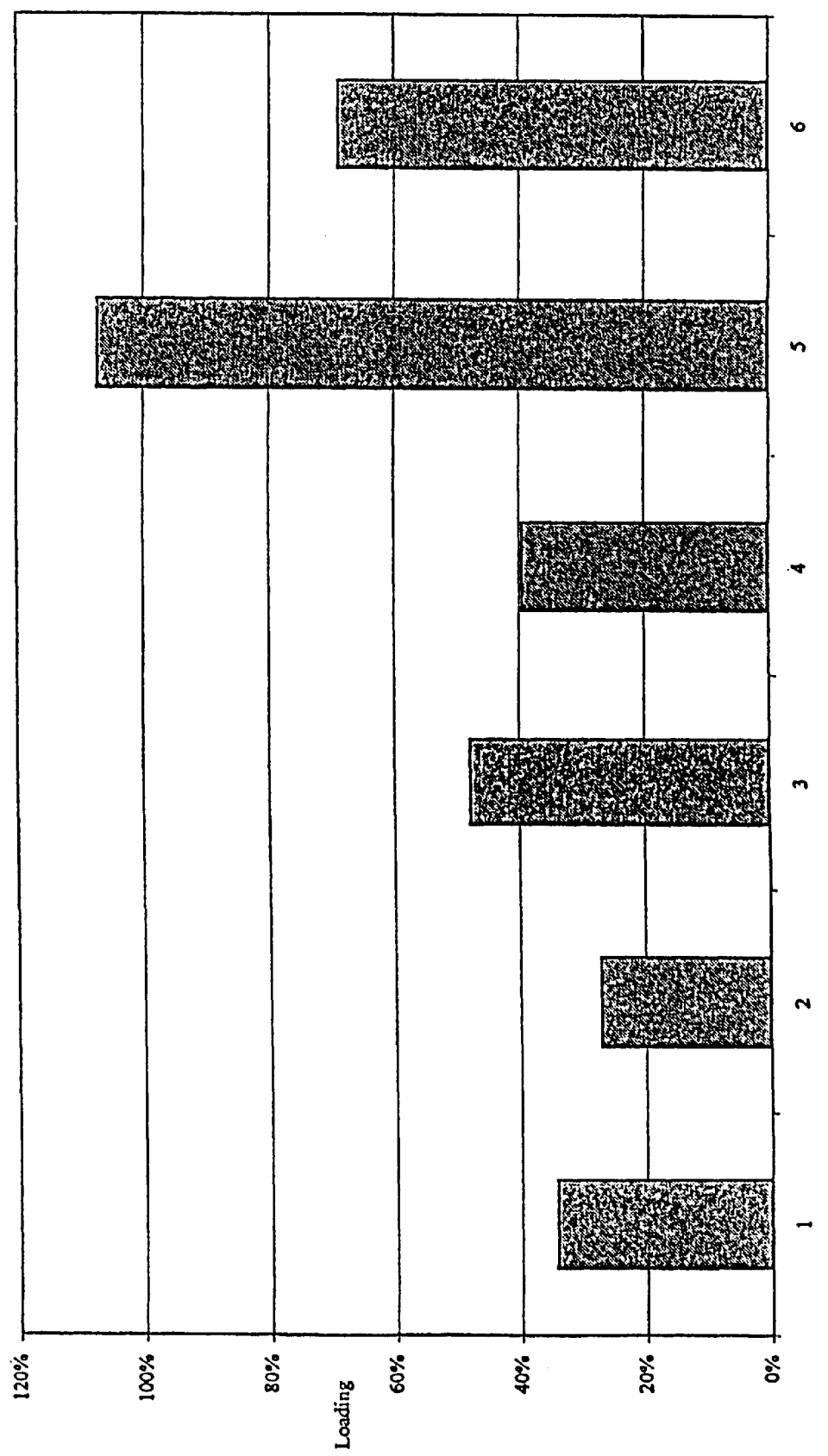
FIG. 6. Loading of acetaminophen into keratin tablets. Loading based on amount used in ion exchange process.
Figure 7:
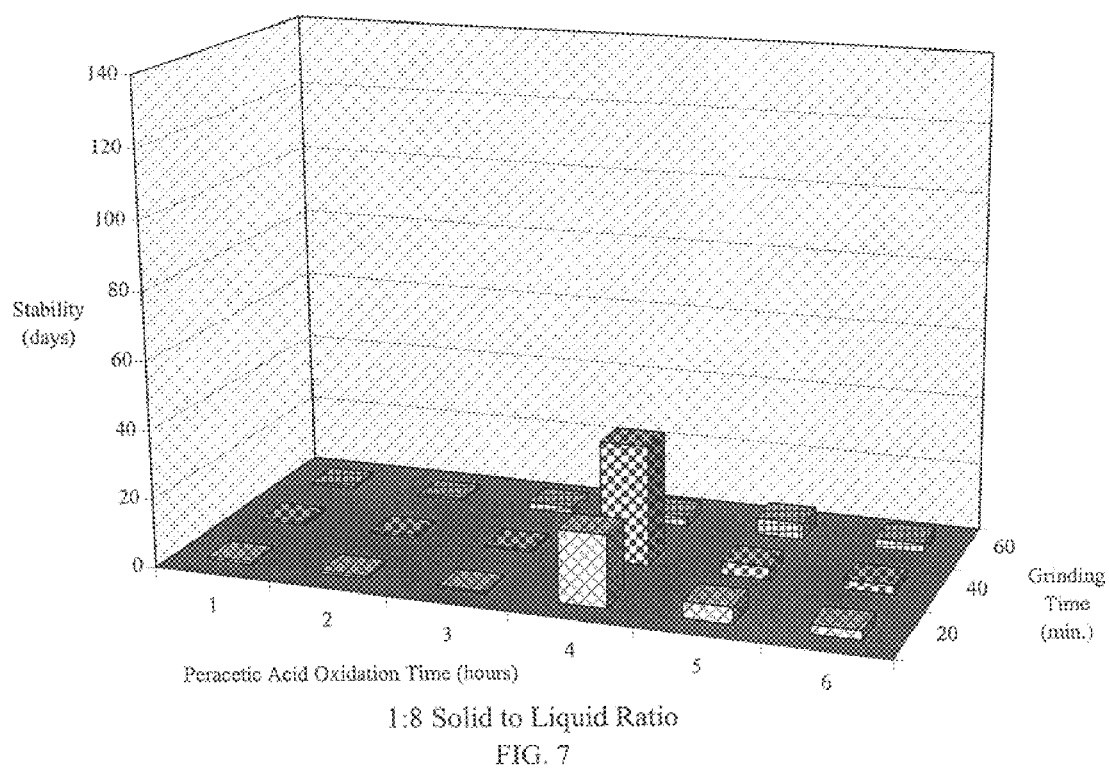
FIG. 7. Stability of keratin hydrogel prepared by peracetic acid oxidation and at a solid to liquid weight ration of 1:8. Columns of <1 day did not form a gel.
Figure 8:
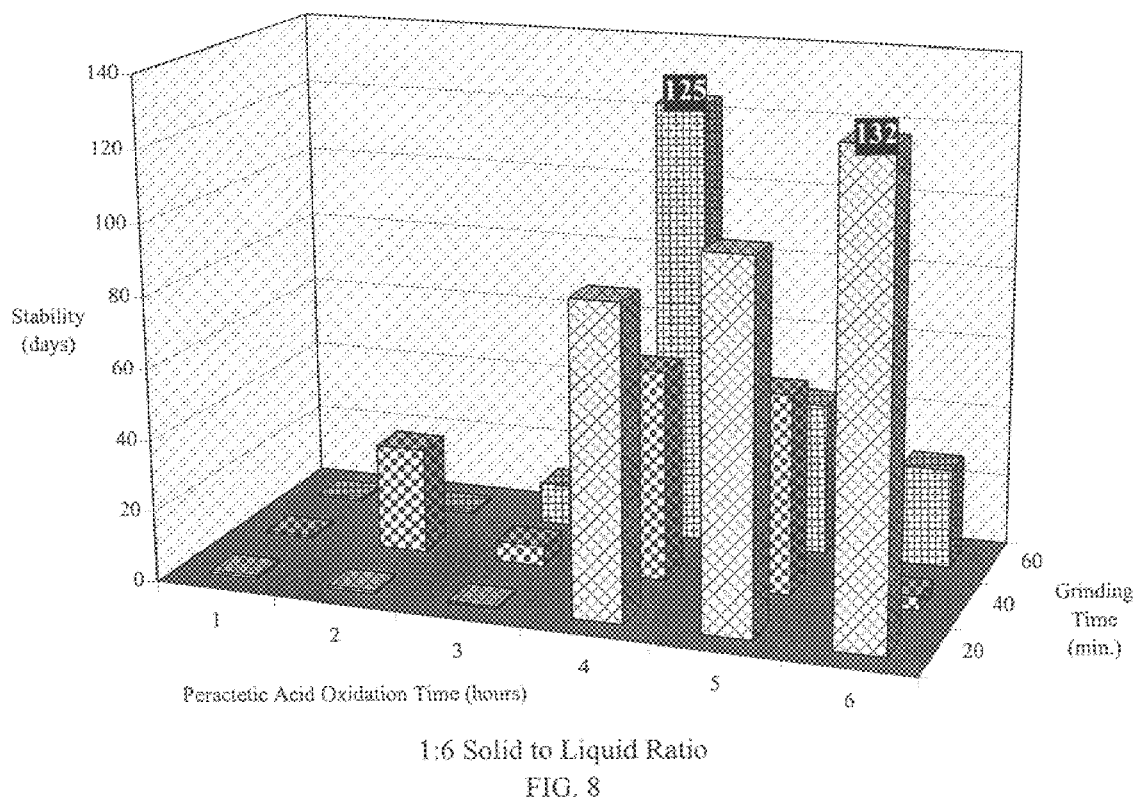
FIG. 8. Stability of keratin hydrogel prepared by peracetic acid oxidation and at a solid to liquid weight ratio of 1:6. Columns of <1 day did not form a gel. Columns with data labels indicate gel stable at last observation point.
Figure 9:
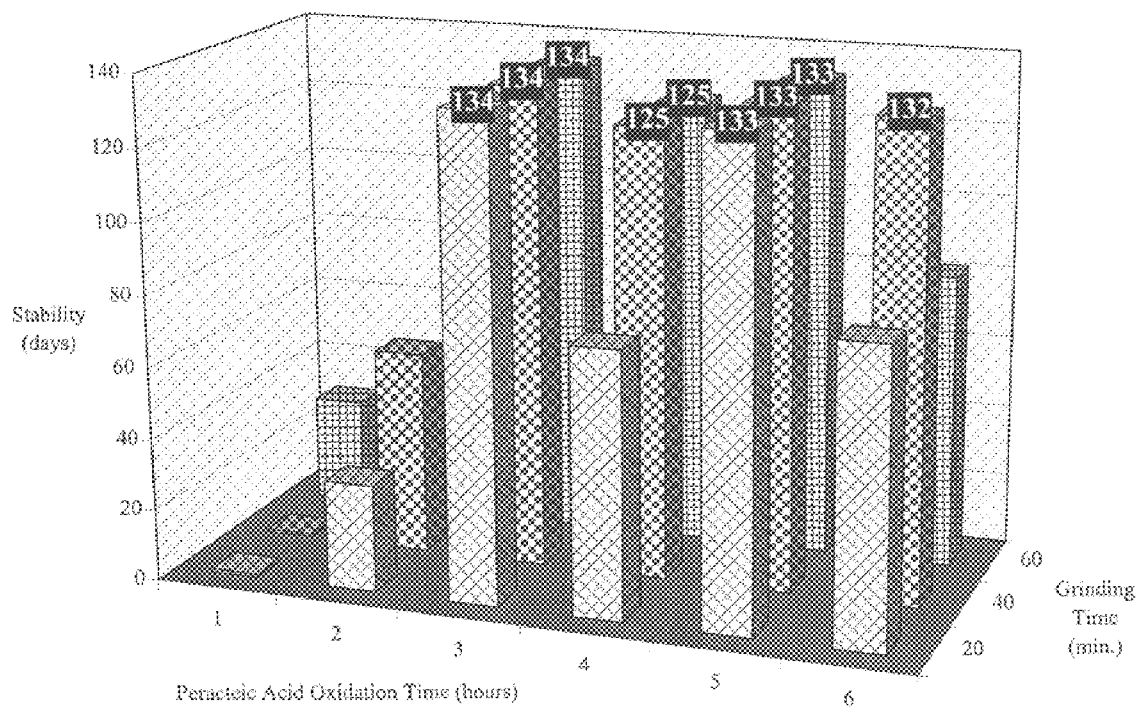
FIG. 9. Stability of keratin hydrogel prepared by peracetic acid oxidation and at a solid to liquid weight ratio of 1:4. Columns of <1 day did not form a gel. Columns with data labels indicate gel stable at last observation point.
Figure 10:
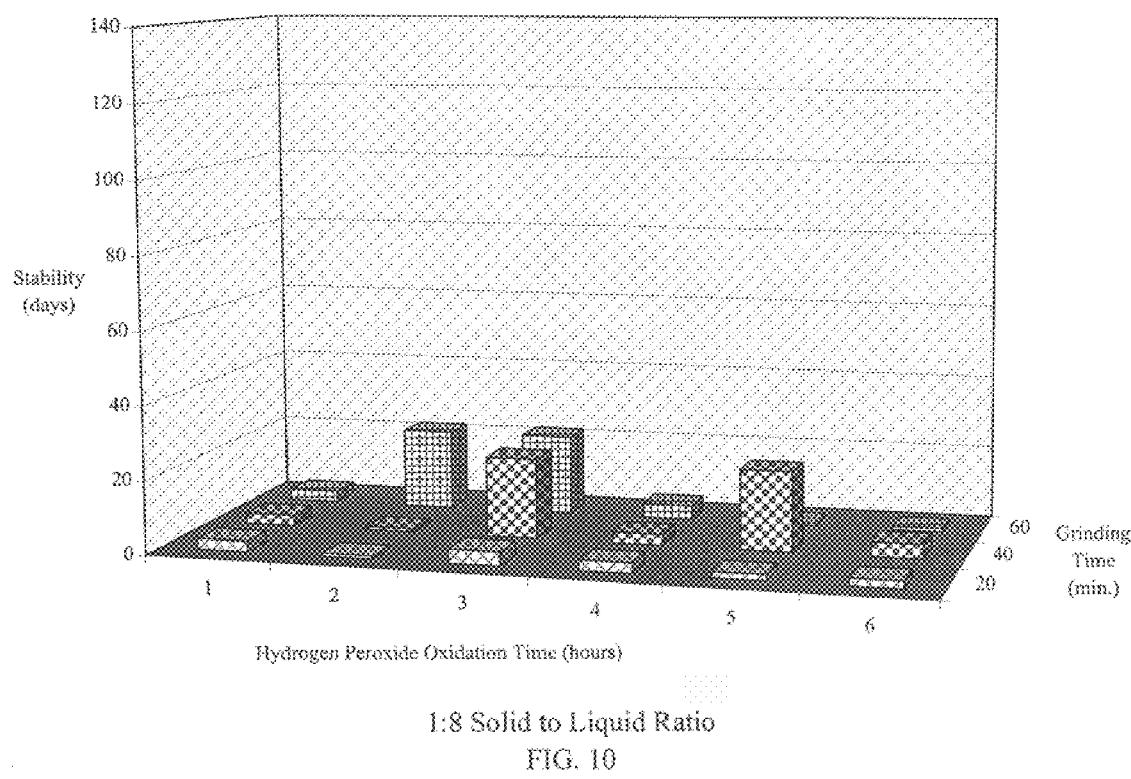
FIG. 10. Stability of keratin hydrogel prepared by hydrogen peroxide oxidation and at a solid to liquid weight ratio of 1:8. Columns of <1 day did not form a gel.
Figure 11:
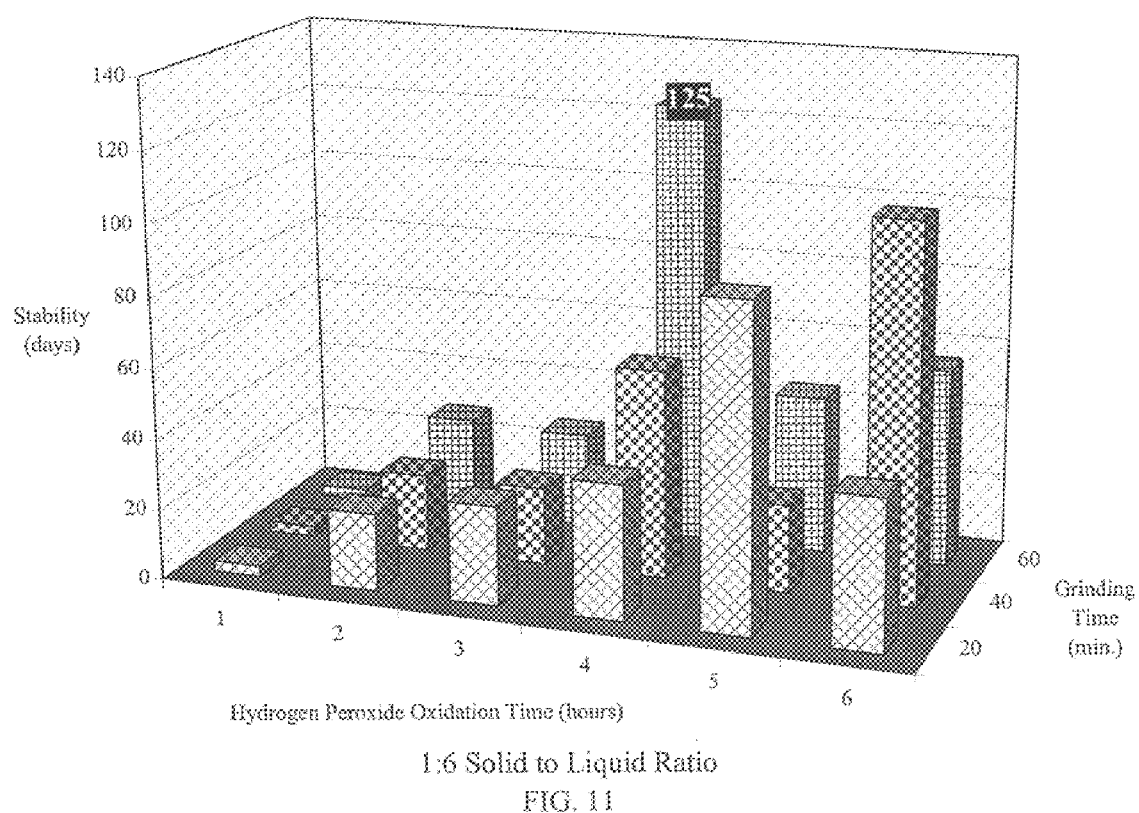
FIG. 11. Stability of keratin hydrogel prepared by hydrogen peroxide oxidation and at a solid to liquid weight ratio of 1:6. Columns of <1 day did not form a gel. Columns with data labels indicate gel stable at last observation point.
Figure 12:
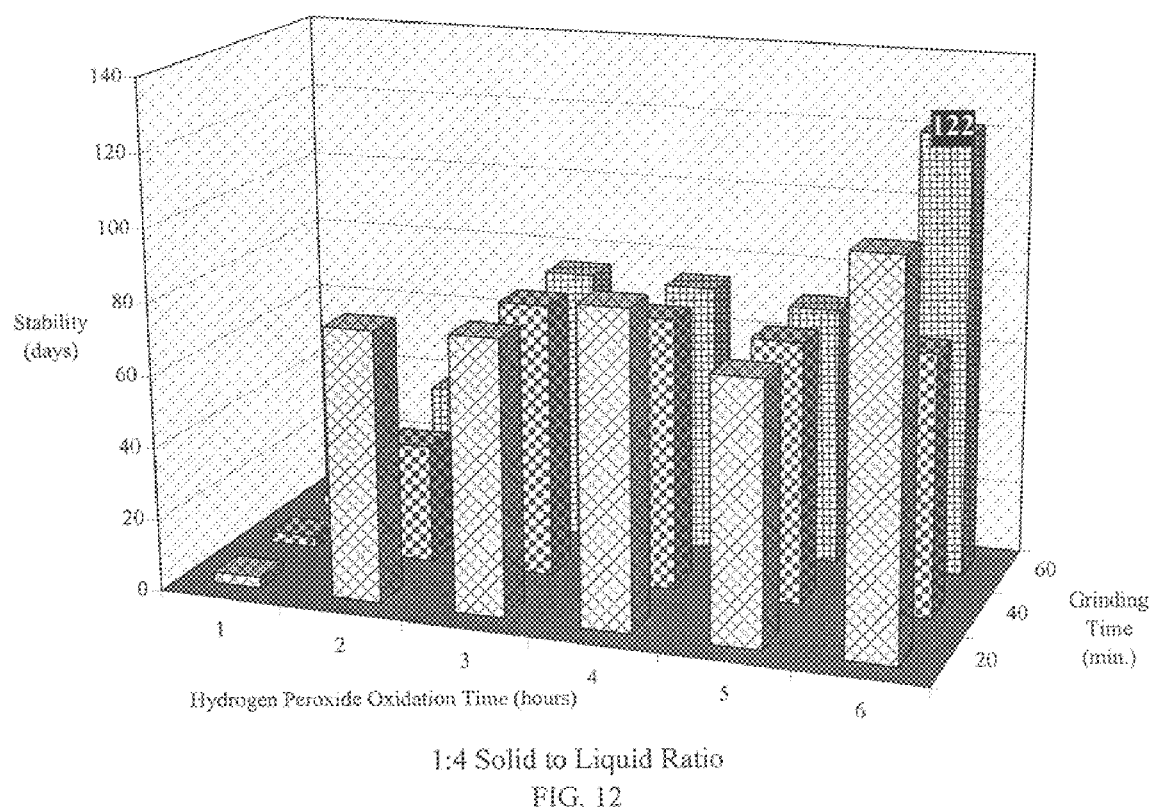
FIG. 12. Stability of keratin hydrogel prepared by hydrogen peroxide oxidation and at a solid to liquid weight ratio of 1:4. Columns of <1 day did not form a gel. Columns with data labels indicate gel stable at last observation point.

The data are shown in FIG. 5. The curves in FIG. 6 do not suggest a clear release trend relative to keratin oxidation time. This may be due to the fact that acetaminophen is a multifunctional molecule and can potentially bind through more than one mechanism. However, these mechanisms do not appear to result in tremendously strong interactions, or large numbers of interactions between acetaminophen and keratin. This is suggested by the overall low loading levels as shown in FIG. 6. The drug compound that does become bound, however, is released at a much slower rate than norephedrine (5 hours versus 2 hours respectively). This is particularly true for the 4-hour oxidation sample.

5. Formulations

The following formulations are examples of the types of formulations in which a keratin excipient of the present invention may be formulated. Formulations, however, are not limited to the following non-exclusive list and a keratin excipient of the present invention may be formulated in any appropriate formulation which may be identified by one of ordinary skill in the art without undue experimentation.

(a) Liposomes

Techniques for producing unilamellar liposomes and multilamellar liopsomes are disclosed in U.S. Pat. Nos. 4,837,028, 4,522,803, 4,501,728, 4,310,506, 4,235,871, 4,224,179, 4,078,052, 4,394,372, 4,308,166, 4,485,054 and 4,508,703 (all herein incorporated by reference). Methods of production of liposomes are also reviewed in Szoka, et al., (1980). A keratin excipient of the present invention may be incorporated in a liposomal preparation such that the preparation comprises about 0.5, or about 1.0 or about 5.0, or about 10, or between about 0.5 to about 5.0, or between about 1 to about 10 percent by weight of the keratin excipient.

(b) Water-in-oil emulsion

Following is an exemplary water-in-oil type emulsion formulation:

| A. | Mixture of a higher molecular fatty alcohol, wax esters and fats | 20.00% |
|---|---|---|
|   | Decyl oleate | 10.00% |
|   | White petroleum jelly | 10.00% |
|   | Triglycerol mixture of various natural fats | 10.00% |
|   | p-Hydroxybenzoic acid propyl ester | 0.02% |
| B. | Water | 49.08% |
|   | Dehydracetate | 0.20% |
|   | p-Hydroxybenzoic acid methyl ester | 0.20% |
| C. | Keratin excipient | 1.00% |
| D. | Perfume oil | 0.50% |

The components mentioned under part A are mixed and warmed to 70° C. Mixture B is boiled up, cooled to 75° C. and added to part A, whilst stirring. Whilst stirring, the mixture is cooled to 35° C. and, parts C and D are added. Amounts given as percentage by weight.

(c) Oil-in-water type emulsion

Following is an exemplary oil-in-water emulsion:

| A. | Self-emulsifying mixture of monoglycerides and diglycerides of higher, saturated fatty acids | 16.00% |
|---|---|---|
|   | Fatty alcohol polyglycol ether | 1.00% |
|   | 2-Octyldodecanol | 6.00% |
|   | Isopropyl myristate | 4.00% |
|   | p-Hydroxybenzoic acid propyl ester | 0.02% |
| B. | Glycerol | 6.00% |
|   | Water | 65.08% |
|   | Na dehydracetate | 0.02% |
|   | p-Hydroxybenzoic acid methyl ester | 0.02% |
| C. | Keratin excipient | 1.00% |
| D. | Perfume oil | 0.05% |

Preparation similar to subsection 4.b supra. Amounts given as percentage by weight.

(d) Cream formulation

Following is an exemplary cream formulation:

| A. | Sodium cetylstearyl sulphate | 0.8% |
|---|---|---|
|   | Cetylstearyl alcohol | 7.2% |
|   | Wool grease | 2.0% |
|   | Isopropyl palmitate | 14.5% |
|   | 2-Octyl-dodecanol | 10.0% |

-continued

| B. | Water (demineralised) | 59.5% |
|---|---|---|
|   | Propylene 1,2-glycol | 5.0% |
| C. | Keratin excipient | 1.0% |
| D. | Perfume oil | 9.5% |
|   | Preservative | 9.5% |

Preparation similar to subsection 4.b supra. Amounts given as percentage by weight.

(e) Lotion formulation

Following is an exemplary lotion formulation:

| A. | Decyl oleate | 2.5% |
|---|---|---|
|   | Isopropyl myristate | 2.5% |
|   | Liquid paraffin | 4.0% |
|   | Polyoxyethylene stearate | 0.9% |
|   | Sorbitane monostearate | 0.6% |
| B. | Water (demineralised) | 80.4% |
|   | Ethyl alcohol | 10.0% |
|   | Allantoin | 0.1% |
| C. | Keratin excipient | 1.0% |
| D. | Perfume oil | 8.5% |
|   | Preservative | 8.5% |

Preparation similar to subsection 4.b supra. Amounts given as percentage by weight.

The formulation of a keratin excipient of the present invention is not limited to 1.0 percent by weight as shown in the exemplified emulsion, cream, or lotion formulations. The keratin excipient may be formulated at any appropriate percentage which may be, but not limited to, about 0.5, or about 1.0, or about 5.0, or about 10.0, or between about 0.5 to about 5.0, or between about 1.0 to about 10.0 percent by weight of the keratin excipient.

E. Cell Scaffold and Tissue Engineering Applications

The use of implantable organ or tissue equivalents has been the subject of considerable research and development. One approach is to attach isolated cells onto biocompatible scaffolds in vitro and then implant the polymer-cell scaffold into recipients (Vacanti, 1988). Methods and examples of the preparation of scaffolds and their use to implant diverse cell types are disclosed in U.S. Pat. Nos. 5,041,138, 5,736,372, 5,759,830, 5,770,193, 5,770,417, 5,964,807, 5,916,557 and 5,981,825, which are herein incorporated by reference. An alternative to the growth of cells on a scaffold in vitro for subsequent implantation, is the use of scaffolds to provide matrices for the infiltration and growth of endogenous cells in vivo. Examples of such are disclosed in U.S. Pat. Nos. 4,772,287 and 4,904,260, which are herein incorporated by reference. Thus tissue engineering scaffolds can be used for tissue repair, tissue reconstruction and wound healing, as disclosed for hyaluronan based scaffolds in U.S. Pat. No. 5,939,323, herein incorporated by reference.

Various hydrogels have been used to form three-dimensional scaffolds suitable for tissue engineering. These include hydrogels made from 2-hydroxyethyl methacrylate (Plant et al., 1995; Santin et al., 1996), agarose (Bellamkonda et al., 1995, Dillon et al., 1998; Yu et al., 1999), gelatin (Kang et al., 1999), alginates (de Chalain et al., 1999; Rowley et al., 1999), and polysaccharide augmented glycosaminoglycan (Sechriest et al., 2000). In addition to the formation of a scaffold to guide growth, injection of cells in hydrogels have been shown to be retained at the delivery site and promote formation of the desired regenerated tissue (Atala et al., 1993; Cao et al. 1998).

Keratins supply suitable substrata for the growth of cells. A keratin sheet has been disclosed to support the proliferation of human keratinocytes, fibroblasts and microvascular endothelial cells (U.S. Pat. No. 5,932,552). In addition, it has been shown that a keratin-coated substrata was more adhesive to fibroblasts than comparative collagen or glass substrata (Yamauchi et al., 1998). A keratin implant material has been disclosed in U.S. Pat. No. 5,358,935, which is herein incorporated by reference. The keratin hydrogel of the present invention provides a suitable material for the construction of cell scaffolds. For example, the absorbent keratin, which into a hydrogel upon the addition of water, can be used in the nonwoven film embodiment of the present invention. The nonwoven film may be constructed with synthetic polymer webs, the synthetic polymers of which may be resorbable. A number of synthetic polymers have been disclosed as suitable structural materials for tissue engineering scaffolds, such as in U.S. Pat. Nos. 5,399,665, 5,981,825, 5,981,825, and 6,022,828, which are herein incorporated by reference. In other embodiments of the present invention, the absorbable keratin powder may be incorporated into synthetic polymer fibers or other three dimensional shapes.

The keratin hydrogel of the present invention may be used as a vehicle for the injection of cells into a specific tissue location. For such a vehicle, the absorbent keratin powder of the present invention would be hydrated water or a medium suitable to maintain cell viability. Such media are well known to those of ordinary skill in the art. Media can be added to the absorbent keratin powder to tailor the viscosity for injection. This viscosity will vary on the gauge size of the needle employed and can be readily ascertained without undue experimentation by one of skill in the art. The injectable keratin hydrogel can also be delivered to a support structure, which may be a permeable support structure, as disclosed in U.S. Pat. No. 6,027,744, hereby incorporated by reference. The injectable keratin hydrogel can also be used as an in vivo scaffold to fill soft tissue structural defects and replace tissue. The keratin hydrogel of the present invention is non-toxic and biocompatible and may be used as a vehicle for various cell types, including, but not limited to keratinocytes, fibroblasts, chondrocytes, hepatocytes, splenocytes, osteoblasts, neurocytes and endothelial cells.

F. Hydrogel Stability

The stability of keratin hydrogels at body temperature was evaluated for drag delivery, injectable implant and tissue engineering applications. The testing matrix employed varied keratin absorbent processing and formulation parameters. Processing parameters that were varied included oxidation time (1–6 hr.), type of oxidant used peracetic acid or hydrogen peroxide), and grinding time, which effected a change in the particle size. Formulation parameters that were varied included solids content of the gel (1:8, 1:6 and 1:4 solids to liquid).

1. Preparation of Hydrogels

The hydrogels were prepared as follows. Human hair obtained from a barbershop was washed with VersaClean™ detergent and dried by vacuum filtration. The hair was oxidized by boiling in 2 w/v % solutions of oxidant (either peracetic acid or hydrogen peroxide) at a solids to liquid ratio of ca. 1:17 for 1, 2, 3, 4, 5 and 6 hours. The oxidized hair was rinsed with deionized water, filtered and dried. The pH of the hair was titrated to ca. 7 by exposure to a known amount of sodium hydroxide. The number of moles of sodium needed to neutralize the oxidized hair was determined from titration curves for peracetic acid and hydrogen peroxide treated hair. Titration was affected by boiling the hair in a solution of ethanol with sodium hydroxide for a 2 hour period. After cooling, the solution was continually stirred for an additional 22 hours. The solid keratin was separated by filtration, rinsed with ethanol and dried under vacuum.

Grinding was performed in a 1-quart ball mill using 1 cm diameter ceramic grinding media. Grinding times of 20, 40 and 60 minutes were used so as to generate smaller keratin particles with longer grinding times. This resulted in the generation of 36 absorbent keratin powder samples (2 oxidants×6 oxidation times×3 grinding times=36 samples). Each powder sample was then used to make hydrogels using pH 7.4 phosphate buffered saline solution (lot no. 099H6118, [120 mmol/L NaCl, 2.7 mmol/L KCl and 10 mmol/L phosphate buffer], Sigma Diagnostics, St. Louis, Mo. 63178). The weight ratio of solids to liquid was varied at 1:8, 1:6 and 1:4, resulting in the generation of 108 samples (2 oxidants×6 oxidation times×3 grinding times×3 gels=108 samples). The gels were mixed in 4 dram vials using a vortex mixer, capped, sealed with Parafilm™ and placed in a heated oven at 37.5° C.±2° C. for in vitro stability testing. Samples that did not form viscous gels were immediately removed from the oven and discarded. Visual observations were conducted on a daily basis throughout the study. Gels that exhibited a decrease in their original viscosity were removed from the study and deemed to no longer be stable. These samples were retained frozen for later analysis.

2. Stability and Viscosity Results

During the preparation of these gels, a variety of viscosities in the resulting hydrogels were observed. In general, gels with higher solids content were more viscous than gels with lower solids content (1:4>1:6>1:8). In addition, shorter grinding times (i.e. larger particle size) also resulted in higher viscosities (20 min.>40 min.>60 min.).

The stability data collected are summarized in the attached FIGS. 7 through 12. Formulations that were not stable for at least one day were categorized as non gelforming as indicated on the graphs. Most samples that were stable for greater than 80 days do not represent the terminus of the test, simply the cutoff point for data collection. To further examine stability, the samples are further observed for greater than 80 days until the samples are no longer stable or until some defined time. Samples which were stable at the last data collection time point are indicated with a data label on the graph.

In general, these data suggest that more stable gels were generated from peracetic acid oxidized hair than from hydrogen peroxide oxidized hair (11 gels with stability greater than 120 days for peracetic acid versus 2 for peroxide). Secondly, gels with higher solids content appear to be more stable. Many more 1:4 gels were stable for long time periods than gels with a lower solids content. Lastly, these data do not show any direct correlation between gel stability and particle size (i.e. grinding time).

In this study 19 gels exceeded 80 days of stability and 13 gels exceeded 120 days of stability. To further test these samples, they are further subjected to elevated temperature testing. Primarily, they are gels made from hair that had been oxidized with peracetic acid for 3, 4 or 5 hours and formulated as 1:4 gels.

These data establish that keratin hydrogels can be processed to remain stable at human body temperature for time periods ranging from days to in excess of four months. At the time of degradation, the gel becomes hydrolyzed to lower molecular wight polypeptides, some in the range of 1000 daltons, and likely becomes bioresorbable. Those gels that do not degrade are likely to remain biostable, thus demonstrating a range of biodegradation and resorption possibilities with these gel formulations. In addition, the gels can be formulated to significantly vary viscosity, ranging from very fluid at low solids concentrations to highly viscous at high solids concentrations.

G. Applications of Hydratable Keratin

One use for the keratin powder and fiber is as a disposable diaper filler material. Disposable diapers typically have an absorbent inner layer that is often filled with a superabsorbent polymer and cellulosic material, often chemically derived from wood pulp. In one application of the keratin material, a layer of the hydratable keratin is positioned in a disposable diaper near the skin but separated from the skin by a permeable layer. The hydratable keratin layer can serve to absorb urine and water from the wearer. In some embodiments, the hydratable keratin includes a substantial fraction of soluble peptides having wound healing properties, as discussed in co-pending U.S. patent application Ser. No. 09/330,550, filed Jun. 11, 1999, entitled SOLUBLE KERATIN PEPTIDE, herein incorporated by reference. The water-soluble peptides are believed to be entrained in the keratin structure and able to leach out when water is applied. In use, the keratin layer remains dry until soaked with urine, at which point the soluble peptides can diffuse out of the keratin. The soluble peptides dissolved in the liquid present can thus come in contact with the skin. The wound healing properties of the peptides are believed to be beneficial in treating diaper rash.

In another use, the hydratable keratin powder or fiber can be used as an ingredient in cosmetics. In one application, the keratin powder is admixed with other cosmetic ingredients. The keratin power, when brought into contact with water from the other cosmetic ingredients or from the skin of the wearer, forms a hydrogel that forms a protective layer over the skin and also retains moisture against the skin. The keratin powder, which has beneficial properties for skin, is thus held against the skin, moisturizing the skin. In some embodiments, the keratin powder includes soluble peptides that can diffuse out of the powder with application of water. The soluble peptides are believed to be non-immunogenic, mitogenic, biocompatible and have beneficial skin healing properties. Cosmetics including the hydratable keratin powder can aid in both moisturizing and healing skin. Keratin powder can also be used as an absorbent replacement to talc, the most popular cosmetic base, to which many are allergic. The keratin powder or fibrous material can be used to promote healing of damaged skin. The keratin material can be applied to skin afflictions such as diaper rash, burns, sunburns, cuts, abrasions, punctures, sores, bed sores, ulcers, diabetic ulcers, irritated skin, surgical incisions, skin graft donor sites, and wrinkled skin. In one method, the keratin material is admixed with a carrier such as a cream, lotion, or gel.

Other applications of the keratin solid include using the keratin powder or fibers in feminine hygiene products, where the keratin can serve a moisture absorbing function. Yet another application is in anti-perspirants, where the keratin solid can absorb moisture. Still another application is in drug release applications, where the keratin can be used in powder, fiber, or film form to provide a moist, benign environment against the skin for drug release. The present invention, in powder, fiber, and nonwoven sheet forms, is also believed suitable for use in forming tissue-engineering scaffolds. An additional use as a food additive is contemplated, as some naturally-derived products, such as gelatin, are already used in food products.

The keratin can also be used as the precursor to the formation of a gel, which can form a keratin hydrogel upon the addition of water to the absorbent keratin solid. The keratin can be used to form an in situ gel. In the in situ application, the keratin powder can reside within an envelope predisposed at a site and the water added into the envelop already in position. The keratin can be stored in solid form, for example as a fiber, powder, or some combination thereof, and water added later. Keeping the keratin in solid form allows for storage and later gel formation only when desired, as in an emergency medical field dressing application. Requiring the keratin to pass through a solid step also serves to purify the resulting gel, as many impurities are removed in the intermediate processing steps.

The present invention can also be used to augment soft tissue. Keratin hydrogel precursor in powder form may be suspended in an injectable carrier and injected subdermally. In one method, the keratin powder is suspended in saline and injected subdermally.

The resulting hydrogel has been observed to have viscoelastic properties, favorable for use as an implant filler such as a breast implant. The hydrogel has been observed to flow more readily when manipulated, which may prove beneficial to implant applications where the consistency of the implant is important.

The present invention can be used in a wound dressing. One use of hydratable keratin in a wound dressing is wound exudate management. Thus hydratable keratin may be used as a component of an absorbent wound dressing. In one embodiment, the hydratable keratin may be used in the form of a nonwoven film. In another embodiment, hydratable keratin may be used as a woven composition. In a woven composition, fibers of hydratable keratin may be woven with natural fibers or synthetic polymer fibers. In another embodiment, hydratable keratin is enclosed by a water-permeable material which, while allowing passage of wound exudate and blood, prevents passage of the hydratable keratin solid of the present invention. Wound dressings include, but are not limited to, adhesive bandages and tapes. Skin-contact adhesive bandages and medical tapes are well known to those of skill in the art. Adhesive bandages typically comprise an absorbent pad, a backing and a pressure sensitive adhesive to maintain the dressing in place. In one aspect of the present invention, an absorbent wound dressing comprising hydratable keratin is an absorbent pad of an adhesive bandage. Components, configurations and delivery systems for adhesive bandages are disclosed in U.S. Pat. Nos. 6,018,092, 5,947,917, 5,633,070, and 5,503,908, which are herein incorporated by reference. Upon contact with moisture, which may be in the form of wound exudate or blood, the keratin fibers can form a hydrogel and leach water soluble peptides into the wound.

Numerous advantages of the invention covered by this document have been set forth in the foregoing description. It will be understood, however, that this disclosure is, in many respects, only illustrative. Changes may, be made in details, particularly in matters of reagents, concentrations, and step order, without exceeding the scope of the invention. The invention's scope is, of course, defined in the language in which the appended claims are expressed.

REFERENCES

The following references, to the extent that they provide exemplary procedural or other details supplementary to those set forth herein, are specifically incorporated by reference.

Agrawal, *J. Biomed. Res. App. Biomaterials*, 38: 105–14 (1997).
Atala et al., *J. Urol.* 150:745–47 (1993).
Bellamkonda et al., *J. Biomed. Mater Res.*, 29:663–71 (1995).
Cao et al., *Plast. Reconstr. Surg.*, 102:2293–98 (1998).
De Chalain et al.,*J. Biomed. Mater Res*, 44:280–288 (1999).
Dillon et al., *J. Biomatter. Sci. Polymer Ed.*, 9:1049–69 (1990).
Duranti et al., *Dermatol. Sugery*, 24:1317–25 (1998).
Flory, Principles of Polymer Chemistry, pp. 497–539, Cornell University Press, Ithaca and London (1953).
Franz, *Curr. Probl. Dermatol.*, 7:309, 1978.
Kang et al., *Biomaterials*, 20: 1339–44 (1999).
Lee et al., *Drug Dev. Indust. Pharm.*, 12:349, 1986.
Manna et al., *J. Eur. Acad. Dermatol. Venereol*, 13:183–92 (1999).
Plant et al., *Brain Res.* 6:119–130 (1995).
Rowley et al., *Biomaterials*, 20:45–53 (1999).
Santin et al., *Biomaterials*, 17:1459–67 (1996).
Sechriest et al., *J. Biomed. Matter Res.*, 49:534–41 (2000).
Szoka, et al., *Ann. Rev. Biophys. Bioeng.*, 9:465–508, 1980.
Vacanti, *Archives of Surgery*, 123: 545–549 (1988).
Yamauchi et al.,*J. Biomater Sci Polym Ed*, 9:259–70, 1998.
Yu et al., *Tissue Eng.* 5:291–304 (1999).

What is claimed is:

1. A preparation comprising a cross-linked insoluble keratin excipient associated with a pharmaceutical or cosmestic active agent, where said keratin excipient is chemically modified to contain sulfonate groups.

2. The preparation of claim 1, wherein said keratin is derived from hair, fur, nails, feet, beaks, feathers, horns or hooves.

3. The preparation of claim 1, wherein said keratin is derived from hair.

4. The preparation of claim 3, wherein said hair is human hair.

5. The preparation of claim 1, wherein said sulfonate groups are ionically associated with cations.

6. The preparation of claim 5, wherein said cations comprise the cationic form of an active agent.

7. The preparation of claim 6, wherein said cations comprise monovalent cations.

8. The preparation of claim 7, wherein said monovalent cations comprise sodium or potassium.

9. The preparation of claim 1, wherein said active agent is the free base of an active agent that may be otherwise formulated as a hydrochloride.

10. The preparation of claim 1, wherein said active agent is a pharmaceutical agent.

11. The preparation of claim 10, wherein said pharmaceutical agent is a protein, polypeptide or peptide.

12. The preparation of claim 1, wherein said active agent is a cosmetic agent.

13. The preparation of claim 12, wherein said cosmetic agent is a water soluble peptide derived from keratin.

14. The preparation of claim 1, wherein said preparation comprising a keratin excipient is prepared in a form selected from the group consisting of a powder, tablet, film, capsule, lotion, cream, gel, solution, suspension, emulsion and aerosol.

15. The preparation of claim 1, wherein said preparation comprising a keratin excipient is prepared in the form of a non-woven film.

16. The preparation of claim 1, further comprising at least one additive selected from the group consisting of diluents, fillers, lubricants, stabilizers, binders and gelants.

17. The preparation of claim 1, wherein association of said active agent with said keratin excipient provides for the controlled release of said active agent.

18. The method of claim 17, wherein the ionic association of said active agent with said keratin excipient provides for the controlled release of said active agent.

19. The preparation of claim 17, wherein the hydrolysis of said keratin excipient provides for the controlled release of said active agent.

20. The preparation of claim 7, wherein said keratin excipient comprises a hydratable keratin.

21. The preparation of claim 1, wherein said keratin excipient is a keratin hydrogel.

22. An absorbent wound dressing comprising the keratin excipient of claim 1.

23. The absorbent wound dressing of claim 22, wherein said absorbent wound dressing is the absorbent pad of an adhesive bandage.

24. A drug delivery device comprising the keratin excipient of claim 1.

25. The device of claim 24, wherein said device is a transdermal drug delivery device.

26. The device of claim 24, wherein said device is an inhalation drug delivery device.

27. The device of claim 24, wherein said device is an oral drug delivery device.

28. The device of claim 24, wherein said device is an implantable drug delivery device.

29. A method for the delivery of a pharmaceutical or cosmetic active agent comprising providing an active agent in a cross-linked insoluble keratin excipient, wherein said keratin excipient contains sulfonate groups.

30. The method of claim 29, wherein said keratin is obtained from hair, fur, nails, feet, beaks, feathers, horns or hooves.

31. The method of claim 29, wherein said keratin is obtained from hair.

32. The method of claim 31, wherein said hair is human hair.

33. The method of claim 29, wherein said active agent is ionically associated with said sulfonate groups.

34. The method of claim 29, wherein said keratin excipient is delivered to the lungs of an animal by inhalation of particles of said keratin excipient.

35. The method of claim 29, wherein said keratin excipient particles are less than about 1 micron in diameter.

36. The method of claim 29, wherein said delivery is transdermal delivery.

37. The method of claim 29, wherein said delivery is oral delivery.

38. The method of claim 29, wherein said keratin excipient is implanted.

39. The method of claim 29, wherein said delivery of said active agent provides for the controlled delivery of said active agent.

40. The method of claim 33, wherein the ionic association of said active agent with said keratin excipient provides for the controlled release of said active agent.

41. The method of claim 29, wherein hydrolysis of said keratin excipient provides for the controlled release of said active agent.

42. The method of claim 33, wherein the ionic association of said active agent with said cross-linked insoluble oxidized keratin excipient and hydrolysis of said cross-linked insoluble oxidized keratin excipient provide for the controlled release of said active agent.

43. The preparation of claim 1, wherein the keratin is derived from wool.

44. The method of claim 29, wherein the keratin is derived from wool.

45. A drug delivery preparation comprising a cross-linked insoluble keratin powder and a pharmaceutical agent wherein the keratin is chemically modified to contain sulfonate groups, and further wherein the keratin powder forms a hydrogel upon absorption of water.

46. A preparation comprising a cross-linked insoluble keratin powder and a cosmetic agent, wherein the keratin is chemically modified to contain sulfonate groups.

47. A preparation comprising a cross-linked insoluble keratin powder containing sulfonate groups, wherein the preparation further comprises acetaminophen, a tetracycline, a penicillin, a vitamin, an antacid a non-steroidal antiinflammatory agent, an anesthetic, a breath freshener, or a mineral.

48. The preparation of claim 47, wherein said powder forms a hydrogel upon absorption of water.

* * * * *

UNITED STATES PATENT AND TRADEMARK OFFICE
CERTIFICATE OF CORRECTION

PATENT NO. : 6,544,548 B1
DATED : April 8, 2003
INVENTOR(S) : Arlene J. Siller-Jackson et al.

It is certified that error appears in the above-identified patent and that said Letters Patent is hereby corrected as shown below:

Column 35,
Line 29, delete "where" please insert -- wherein --.

Column 36,
Line 10, delete "7" please insert -- 1 --.

Column 37,
Line 4, please insert -- , -- after "agent".

Signed and Sealed this

Fifth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,544,548 B1
DATED : April 8, 2003
INVENTOR(S) : Arlene J. Siller-Jackson et al.

It is certified that error appears in the above-identified patent and that said Letters Patent is hereby corrected as shown below:

Column 36,
Line 4, delete "method" please insert -- preparation --.

Signed and Sealed this

Sixteenth Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO.    : 6,544,548 B1
DATED         : April 8, 2003
INVENTOR(S)   : Arlene J. Siller-Jackson et al.

It is certified that error appears in the above-identified patent and that said Letters Patent is hereby corrected as shown below:

Column 36,
Line 4, delete "method" please insert -- preparation --.

Signed and Sealed this

Third Day of August, 2004

JON W. DUDAS
*Acting Director of the United States Patent and Trademark Office*

UNITED STATES PATENT AND TRADEMARK OFFICE
CERTIFICATE OF CORRECTION

PATENT NO.    : 6,544,548 B1                                         Page 1 of 1
DATED         : April 8, 2003
INVENTOR(S)   : Arlene J. Siller-Jackson et al.

It is certified that error appears in the above-identified patent and that said Letters Patent is hereby corrected as shown below:

Column 35,
Lines 28-29, delete "cosmestic" please insert -- cosmetic --.

Signed and Sealed this

Twenty-eighth Day of June, 2005

JON W. DUDAS
*Director of the United States Patent and Trademark Office*

UNITED STATES PATENT AND TRADEMARK OFFICE
CERTIFICATE OF CORRECTION

PATENT NO. : 6,544,548 B1
DATED : April 8, 2003
INVENTOR(S) : Arlene J. Siller-Jackson et al.

It is certified that error appears in the above-identified patent and that said Letters Patent is hereby corrected as shown below:

Column 36,
Line 44, delete "29" please insert -- 34 --.

Signed and Sealed this

First Day of November, 2005

JON W. DUDAS
*Director of the United States Patent and Trademark Office*